(12) United States Patent
Fang et al.

(10) Patent No.: US 10,087,260 B2
(45) Date of Patent: Oct. 2, 2018

(54) ANTI-HER2 ANTIBODY AND CONJUGATE THEREOF

(71) Applicant: REMEGEN, LTD., Yantai, Shandong (CN)

(72) Inventors: Jianmin Fang, Yantai (CN); Changjiang Huang, Yantai (CN); Jing Jiang, Yantai (CN); Xuejing Yao, Yantai (CN); Hongwen Li, Yantai (CN); Qiaoyu Xu, Yantai (CN); Zhuanglin Li, Yantai (CN)

(73) Assignee: REMEGEN, LTD., Yantai (CN)

( * ) Notice: Subject to any disclaimer, the term of this patent is extended or adjusted under 35 U.S.C. 154(b) by 0 days.

(21) Appl. No.: 15/037,104

(22) PCT Filed: Nov. 18, 2014

(86) PCT No.: PCT/CN2014/091332
§ 371 (c)(1),
(2) Date: May 17, 2016

(87) PCT Pub. No.: WO2015/074528
PCT Pub. Date: May 28, 2015

(65) Prior Publication Data
US 2016/0304621 A1 Oct. 20, 2016

(30) Foreign Application Priority Data

Nov. 19, 2013 (CN) .......................... 2013 1 0586326

(51) Int. Cl.
*A61K 39/395* (2006.01)
*C07K 16/32* (2006.01)
*A61K 47/68* (2017.01)

(52) U.S. Cl.
CPC .......... *C07K 16/32* (2013.01); *A61K 47/6801* (2017.08); *A61K 47/6855* (2017.08); *C07K 2317/92* (2013.01)

(58) Field of Classification Search
None
See application file for complete search history.

(56) References Cited

U.S. PATENT DOCUMENTS

| | | | |
|---|---|---|---|
| 2008/0311134 A1 | 12/2008 | Junutula et al. |
| 2011/0177095 A1 | 7/2011 | Harding et al. |
| 2011/0177099 A1 | 7/2011 | Lackner et al. |
| 2011/0217305 A1 | 9/2011 | Pedersen et al. |
| 2013/0171148 A1 | 7/2013 | De Goeij et al. |
| 2013/0189271 A1 | 7/2013 | De Goeij et al. |

FOREIGN PATENT DOCUMENTS

| | | |
|---|---|---|
| CA | 2376596 | 10/2009 |
| CA | 2872226 | 11/2013 |
| CN | 101143902 | 3/2008 |
| CN | 101687037 | 3/2010 |
| CN | 102027135 | 4/2011 |
| CN | 102030827 | 4/2011 |
| CN | 103153339 | 6/2013 |
| CN | 103154035 | 6/2013 |
| JP | 2013-529904 | 7/2013 |
| JP | 2013-534809 | 9/2013 |
| RU | 2270029 | 2/2006 |
| WO | WO 2008/150485 | 12/2008 |
| WO | WO 2011/107957 | 9/2011 |
| WO | WO 2011/147982 | 12/2011 |

OTHER PUBLICATIONS

English translation of PCT International Search Report issued in International Application No. PCT/CN2014/091332, dated Feb. 11, 2015.
Office Communication issued in Canadian Patent Application No. 2,919,359, dated Dec. 2, 2016.
Office Communication issued in Japanese Patent Application No. 2016-537121, dated Dec. 2, 2016. (English translation of Japanese text).
Extended European Search Report issued in European Patent Application No. 14864053.5, dated May 16, 2017.
Miao et al.,"An overview of antibody-based cancer therapy," *Acta Pharmaceutica Sinica*, 47(10):1261-1268, 2012. (English abstract of Chinese publication).
Office Communication issued in Chinese Patent Application No. 201480006648.8, dated May 3, 2017. (English translation of Chinese text).
Rockberg et al., "Discovery of epitopes for targeting the human epidermal growth factor receptor 2 (HER2) with antibodies," *Molecular Oncology*, 3:238-247, 2009.
Zhang et al., "The new progress of the study for anti-Her2 monoclonal antibody," *Foreign Medical Sciences, Section of Pathophysiology and Clinical Medicine*, 23(3):257-259, 2003. (English abstract of Chinese publication).
Zhu and Fu, "Design of next generation antibody drug conjugates," *Acta Pharmaceutica Sinica*, 48(7):1053-1070, 2013. (English abstract of Chinese publication).
Office Communication issued in Russian Patent Application No. 2016106339, dated Dec. 12, 2017. (English translation of Russian text.).

*Primary Examiner* — Laura B Goddard
(74) *Attorney, Agent, or Firm* — Parker Highlander PLLC

(57) ABSTRACT

Disclosed are an anti-HER2 antibody and conjugate of the anti-HER2 antibody and small molecule medicine. Also disclosed are uses of the antibody and conjugate thereof in preparing medicine for treating tumor.

19 Claims, 10 Drawing Sheets
Specification includes a Sequence Listing.

A

B

A

B

A

B

SEQUENCE LISTING

```
<160> NUMBER OF SEQ ID NOS: 20

<210> SEQ ID NO 1
<211> LENGTH: 5
<212> TYPE: PRT
<213> ORGANISM: Mus musculus

<400> SEQUENCE: 1

Asp Tyr Tyr Ile His
1               5

<210> SEQ ID NO 2
<211> LENGTH: 17
<212> TYPE: PRT
<213> ORGANISM: Mus musculus

<400> SEQUENCE: 2

Arg Val Asn Pro Asp His Gly Asp Ser Tyr Tyr Asn Gln Lys Phe Lys
1               5                   10                  15

Asp

<210> SEQ ID NO 3
<211> LENGTH: 9
<212> TYPE: PRT
<213> ORGANISM: Mus musculus

<400> SEQUENCE: 3

Ala Arg Asn Tyr Leu Phe Asp His Trp
1               5

<210> SEQ ID NO 4
<211> LENGTH: 11
<212> TYPE: PRT
<213> ORGANISM: Mus musculus

<400> SEQUENCE: 4

Lys Ala Ser Gln Asp Val Gly Thr Ala Val Ala
1               5                   10

<210> SEQ ID NO 5
<211> LENGTH: 7
<212> TYPE: PRT
<213> ORGANISM: Mus musculus

<400> SEQUENCE: 5

Trp Ala Ser Ile Arg His Thr
1               5

<210> SEQ ID NO 6
```

```
<211> LENGTH: 7
<212> TYPE: PRT
<213> ORGANISM: Mus musculus

<400> SEQUENCE: 6

His Gln Phe Ala Thr Tyr Thr
1               5

<210> SEQ ID NO 7
<211> LENGTH: 26
<212> TYPE: DNA
<213> ORGANISM: Artificial Sequence
<220> FEATURE:
<223> OTHER INFORMATION: P1 primer

<400> SEQUENCE: 7
cgggatcctg ccaccagctg tgcgcc                                            26

<210> SEQ ID NO 8
<211> LENGTH: 28
<212> TYPE: DNA
<213> ORGANISM: Artificial Sequence
<220> FEATURE:
<223> OTHER INFORMATION: P2 primer

<400> SEQUENCE: 8
gctctagatc agttgatggg gcaaggct                                          28

<210> SEQ ID NO 9
<211> LENGTH: 22
<212> TYPE: DNA
<213> ORGANISM: Artificial Sequence
<220> FEATURE:
<223> OTHER INFORMATION: mRC48-VL-1 primer

<400> SEQUENCE: 9
gttggtgcag catcagcccg tt                                                22

<210> SEQ ID NO 10
<211> LENGTH: 23
<212> TYPE: DNA
<213> ORGANISM: Artificial Sequence
<220> FEATURE:
<223> OTHER INFORMATION: mRC48-VL-2

<400> SEQUENCE: 10
gttcactgcc atcaatcttc cac                                               23

<210> SEQ ID NO 11
<211> LENGTH: 20
<212> TYPE: DNA
<213> ORGANISM: Artificial Sequence
<220> FEATURE:
<223> OTHER INFORMATION: mRC48-VH-1

<400> SEQUENCE: 11
gccagtggat agacagatgg                                                   20

<210> SEQ ID NO 12
<211> LENGTH: 21
<212> TYPE: DNA
<213> ORGANISM: Artificial Sequence
<220> FEATURE:
<223> OTHER INFORMATION: mRC48-VH-2

<400> SEQUENCE: 12
```

```
aggtcactgt cactggctca g                                              21

<210> SEQ ID NO 13
<211> LENGTH: 31
<212> TYPE: DNA
<213> ORGANISM: Artificial Sequence
<220> FEATURE:
<223> OTHER INFORMATION: VH1 primer

<400> SEQUENCE: 13
cgcggatccg ccgccaccat gggatggagc t                                   31

<210> SEQ ID NO 14
<211> LENGTH: 42
<212> TYPE: DNA
<213> ORGANISM: Artificial Sequence
<220> FEATURE:
<223> OTHER INFORMATION: VH2 primer

<400> SEQUENCE: 14
gatgggccct tggtgctagc ggagctcact gtcaccagtg tt                       42

<210> SEQ ID NO 15
<211> LENGTH: 20
<212> TYPE: DNA
<213> ORGANISM: Artificial Sequence
<220> FEATURE:
<223> OTHER INFORMATION: CH1 primer

<400> SEQUENCE: 15
gctagcacca agggcccatc                                                20

<210> SEQ ID NO 16
<211> LENGTH: 29
<212> TYPE: DNA
<213> ORGANISM: Artificial Sequence
<220> FEATURE:
<223> OTHER INFORMATION: CH2 primer

<400> SEQUENCE: 16
ccggaattct ttaccgggag acagggaga                                      29

<210> SEQ ID NO 17
<211> LENGTH: 32
<212> TYPE: DNA
<213> ORGANISM: Artificial Sequence
<220> FEATURE:
<223> OTHER INFORMATION: VL1 primer

<400> SEQUENCE: 17
cgcggatccg ccgccaccat ggacatgagg gt                                  32

<210> SEQ ID NO 18
<211> LENGTH: 40
<212> TYPE: DNA
<213> ORGANISM: Artificial Sequence
<220> FEATURE:
<223> OTHER INFORMATION: VL2 primer

<400> SEQUENCE: 18
gatggtgcag ccacagtacg ctttatctca acttttgtac                          40

<210> SEQ ID NO 19
<211> LENGTH: 19
<212> TYPE: DNA
<213> ORGANISM: Artificial Sequence
```

```
<220> FEATURE:
<223> OTHER INFORMATION: CL1 primer

<400> SEQUENCE: 19
cgtactgtgg ctgcaccat                                                    19

<210> SEQ ID NO 20
<211> LENGTH: 29
<212> TYPE: DNA
<213> ORGANISM: Artificial Sequence
<220> FEATURE:
<223> OTHER INFORMATION: CL2 primer

<400> SEQUENCE: 20
ccggaattca cactctcccc tgttgaagc                                         29
```

ANTI-HER2 ANTIBODY AND CONJUGATE THEREOF

The present application is a national phase application under 35 U.S.C. § 371 of International Application No. PCT/CN2014/091332, filed Nov. 18, 2014, which claims the benefit of Chinese Patent Application No. 201310586326.2, filed Nov. 19, 2013. The entirety of each of the above-referenced disclosures are incorporated herein by reference.

Pursuant to 37 C.F.R. 1.821(c), a sequence listing is submitted herewith as an ASCII compliant text file named "UNITP0016US_ST25.txt", created on May 17, 2016 and having a size of ~4 kilobytes. The content of the aforementioned file is hereby incorporated by reference in its entirety.

FIELD OF INVENTION

The present invention relates to a novel HER2 antibody or functional fragments thereof, comprising engineered heavy chains and light chains. The present invention further relates to conjugates of the improved HER2 antibody with small molecule drugs. The present invention further relates to use of the antibody and the conjugates in the manufacture of a medicine for treating tumors.

BACKGROUND OF THE INVENTION

1. Summary of HER2

ErbB2, also known as HER2/neu, is the second member of the EGFR family, which forms a heterodimer with other three members in the EGFR family, so as to exert the biological function. To date, the ligand which can directly bind to ErbB2 has not yet been found. The neu gene encoding ErbB2 was firstly separated from rat neuroblastoma. A homologous gene of neu gene in human somatic cells, known as HER2, is located on chromosome 17q21.1. The encoded product is ErbB2, which is consisted of 1255 amino acids with the molecular weight around 185 kDa, in which positions 720-987 belong to tyrosine kinase active domain. In addition to playing a role through PI3K and MAPK signaling pathway, ErbB2 may also reduce the expression of cyclin D and c-myc, thereby reduce the expression of the cyclin-dependent kinase (cdk) inhibitor p27kipl, leading to cell proliferation resulting from the inhibition of cdk2 activity [1].

With the increasingly expanding and deepening studies, it has been found that HER2 is expressed or over-expressed in various tumors. So far, it has been reported that the positive expression rate, over-expression rate of HER2 in several tumors and the number of people within whom HER2 is over-expressed are as follows: ovarian cancer, 45%, 21%, 23316 persons [2]; breast cancer, 58%, 38%, 223112 persons [3]. Hence, there is an urgent need in clinical practice for effective drugs targeting HER2 to treat malignant tumor. Till present, the commercially available monoclonal antibodies which target HER2 include Trastuzumab and Pertuzumab.

2. Trastuzumab and Pertuzumab

Herceptin® (Trastuzumab), developed by Genentech, is a humanized monoclonal antibody which targets HER2. In 1998, Trastuzumab in combination with paclitaxel was approved by the US FDA as a first-line therapeutic regimen for treating HER2/neu over-expressed metastatic breast cancer, or as a single drug for treating HER2/neu over-expressed metastatic breast cancer which had been subjected to at least one cycle of chemotherapy. Trastuzumab not only has high affinity with HER2 receptor, but also solves the problem of immunogenicity caused by applying murine-derived antibody to human body. The results of the clinical trials show that, using Trastuzumab only has the effective rate of 11.6%~16%, while its combination therapy with chemical drugs has the effective rate up to 50%. Comparing with chemotherapy only, said combination confers patients with advanced recurrent breast cancer a longer life span and a reduced mortality.

Another antibody drug which targets HER2 is Pertuzumab [4], which was also developed by Genentech. Pertuzumab binds to region II of the extracellular domain of HER2 receptor, inhibiting the formation of a dimer, thereby inhibiting receptor-mediated signaling pathway, while Trastuzumab (Herceptin) binds to region IV of the extracellular domain of HER2 receptor. Pertuzumab was approved by US FDA on Jun. 8, 2012, for treating HER2-positive advanced metastatic breast cancer patients (see CN101023100B).

3. Antibody-Drug Conjugates

Monoclonal antibody has received more and more attentions due to its characteristics of high target specificity, low side effect and the like. However, when used alone, its therapeutic effect is limited. Now, the most successful monoclonal antibody drugs against tumor are the ones against lymphocytoma such as chronic non-Hodgkin's lymphocytoma (NHL). The Phase II clinical study of Rituxan directed to NHL shows that the total response rate was only 6%. Regarding Herceptin® against metastatic breast cancer, only 15% have a response. Therefore, most of the monoclonal antibody drugs are used in combination with chemotherapy. For example, Rituxan is used in combination with standard chemotherapy for treating chronic lymphocytoma, which may increase the effective rate up to 90%. Till present, the major way for increasing the therapeutic effect of monoclonal antibody is antibody-drug conjugates.

Antibody-drug conjugate belongs to a type of new anti-cancer "biological missile" drug, which is consisted of three parts: antibody, cytotoxin and the linker which links the two parts. Monoclonal antibody is coupled with cytotoxin through chemical coupling. Then the antibody-drug conjugate specifically recognizes the receptor on the surface of cancer cells and binds to the receptor by using the targeting of the monoclonal antibody, and then, the conjugate enters into the cells, and prevents cancer cells from proliferating and kills cancer cells by using proteases in cells which may release the cytotoxin. The antibody-drug coupling technology makes the small molecule drug and biological protein fuse together, which may have the advantages of both and increase the potency of drugs remarkably, reduce the side effects and thus turn into a new generation of therapeutic product.

The first successful example in clinical practice of targeted antibody-drug conjugate is Gemtuzumab ozogamicin (Wyeth, trade name: Mylotarg). Mylotarg is the firstly approved monoclonal antibody-drug conjugate. This drug is consisted of anti-CD33 antibody, Calicheamicin (a drug which degrades DNA) and chemical linker AcBut. Mylotarg is a drug in which a humanized anti-CD33 IgG4 is coupled with antitumor drug Calicheamicin, for treating acute myeloid leukemia [5]. Mylotarg is the first generation of antibody-drug conjugate, which has three critical defects in technology: firstly, the linker used to link toxin is very unstable, the half-life of which is only two days, leading to a severe toxin dropping and a high toxic side effect in clinical practice; secondly, the antibody is coupled with the linker through the amino group of lysine, nevertheless, there are tens of lysines on the surface of an antibody, and the coupling sites are random, which partly affect the potency of drugs; more importantly, since the coupling technology is not mature at that time, only 50% of antibodies may couple with the drug, which results in an unsatisfactory potency of drugs in clinical practice; thirdly, the antibody used is IgG4, which lacks antibody-dependent cell-mediated cytotoxicity (ADCC) and complement dependent cytotoxicity (CDC).

Therefore, ten years after marketing, Mylotarg was withdrawn from the market due to a high toxic side effect and limited therapeutic effect.

The second successful example in clinical practice of targeted antibody-drug conjugate is a novel drug for treating Hodgkin's lymphoma. Since having a very good therapeutic effect, it was approved by US FDA in 2011 after only conducting Phase II clinical trial. This drug was developed by Seattle Genetics as a novel targeted antibody-drug conjugate (ADC), which is a targeted treatment for two types of patients with lymphoma expressing CD30 antigen. This antibody-drug conjugate, brentuximab vedotin, is consisted of monoclonal antibody against CD30, microtubule inhibitor (MMAE) and a dipeptide chemical linker. This antibody-drug conjugate has characteristics of low side effect and effective lymphoma inhibition. In a Phase II single group clinical trial, 102 patients from 15 to 77 years old (median age=31) with recurrent or refractory Hodgkin's lymphoma, received brentuximab vedotin treatment, and the median treatment comprises 9 cycles. When the median treatment course was 6.7 months, the overall response rate was 73%. When the median treatment course was 20.5 months, the complete response rate was 34%; 40% of patients who received the treatment achieved partial response [7]. The most common adverse reaction is peripheral nerve lesion. The success of this drug suggests a technological feasibility and a very bright future of the targeted antibody-drug conjugate.

Another successful example of targeted antibody-drug conjugate is T-DM1 against malignant breast cancer developed by Genentech Inc. [8]. The monoclonal antibody in this antibody-drug conjugate is an anti-HER2 (ErbB2) antibody on the surface of breast cancer cells, which is coupled with the cytotoxin, microtubule inhibitor DM1. The result in Phase III clinical trial of this drug shows better therapeutic effect than chemotherapy, and a lower side effect. Those patients with breast cancer, who have received Herceptin and taxanes chemotherapy drugs treatment previously, still have progressed diseases. However, receiving antibody-drug conjugate treatment may significantly prolong the survival time of those HER2-positive breast cancer patients under the premise of the disease not becoming worse [9]. Based on the good therapeutic effect of this drug, the drug was approved by US FDA on Feb. 22, 2013, for treating HER2-positive advanced metastatic breast cancer patients (see CN100482281C).

Although Herceptin is a breakthrough in the history of the treatment of HER2-overexpressed breast cancer in which various anticancer treatments have already been attempted, about 85% of the subjects have no or only weak response to Herceptin therapy[11]. It has shown that, HER2 is expressed or overexpressed in various tumors. Thus, there is an urgent need in clinical practice for developing anticancer drugs targeting HER2, for those patients with HER2-overexpressed tumors or other HER2-expressed relevant diseases (not just including breast cancer), who have no or only weak response to Herceptin therapy.

Therefore, there is an urgent need in clinical practice for developing a drug targeting HER2. The present invention provides a technical solution to meet this need.

SUMMARY OF THE INVENTION

In one aspect, the present invention provides an antibody or functional fragments thereof which can specifically bind to HER2. Particularly, the antibody comprises a heavy chain and a light chain, in which:

(i) the heavy chain comprises three CDR regions, in which at least one of the CDR regions has the amino acid sequence as shown in SEQ ID NO: 1, 2 or 3 or has at least 80% (preferably, 85%, 90%, 95%, 98% or 99%) sequence identity with SEQ ID NO: 1, 2 or 3; and (ii) the light chain comprises three CDR regions, in which at least one of the CDR regions has the amino acid sequence as shown in SEQ ID NO: 4, 5 or 6 or has at least 80% (preferably, 85%, 90%, 95%, 98% or 99%) sequence identity with SEQ ID NO: 4, 5 or 6.

In a particular embodiment, the antibody comprises a heavy chain and a light chain, in which:

(i) the heavy chain comprises three CDR regions, each of which has the amino acid sequence as shown in SEQ ID NO: 1, 2 and 3, respectively; and/or (ii) the light chain comprises three CDR regions, each of which has the amino acid sequence as shown in SEQ ID NO: 4, 5 and 6, respectively.

In a preferable embodiment, the present invention provides an antibody secreted from the hybridoma cells (deposited at the China General Microbiological Culture Collection Center (located at Institute of Microbiology, Chinese Academy of Sciences, No. 3, 1st Beichen West Rd., Chaoyang District, Beijing 100101, P. R. China) on Aug. 22, 2013, with the deposit number of 8102 (CGMCC No. 8102)) or an antibody derived therefrom (the date of transfer to Budapest Treaty is Oct. 29, 2013). In another preferable embodiment, the present invention provides an antibody secreted from the Chinese hamster ovary (CHO) cells (deposited at the China Center for Type Culture Collection (located at Wuhan University, Luojia Mountain, Wuchang District, Wuhan City, Hubei 430072, P. R. China) on Nov. 6, 2013, with the deposit number of C2013170 (CCTCC C2013170)) or an antibody derived therefrom.

In another aspect, the present invention provides an isolated polynucleotide encoding the antibody of the present invention.

In a further aspect, the present invention provides a combination of the isolated polynucleotides, which comprises the polynucleotide encoding the light chain of the antibody of the present invention or the functional fragments thereof and the polynucleotide encoding the heavy chain of the antibody of the present invention or the functional fragments thereof.

In a further aspect, the present invention provides an expression vector which comprises the polynucleotide according to the present invention or the combination of the polynucleotides according to the present invention, in which the polynucleotide operatively links to a regulatory sequence which allows the polypeptide encoded by the polynucleotide to express in a host cell or a cell-free expression system.

In another aspect, the present invention provides a conjugate comprising the antibody of the present invention or the functional fragments thereof which are coupled with one or more therapeutic agents. Preferably, the therapeutic agent is cytotoxic drug (such as antimetabolites, antitumor antibiotics, alkaloids), immunopotentiators or radioactive isotopes. More preferably, the therapeutic agent is selected from maytansinoids (such as Ansamitocin or Mertansine), dolastatin and derivatives thereof. Most preferably, the therapeutic agent is selected from MMAE (Monomethyl auristatin E) and MMAF (Monomethyl auristatin F). In other embodiments, the therapeutic agent may also be selected from those listed in Table 1 as below.

TABLE 1

List of the available therapeutic agents in the conjugates of the present invention

| Abbreviation | Full Name | Type/Action Mechanism |
|---|---|---|
| MMAE | Monomethyl auristatin E | tubulin monomer polymerization inhibitor[12] |
| MMAE derivative | | |
| MMAE | Monomethyl auristatin E | tubulin monomer polymerization inhibitor[12] |
| MMAF derivative | | |
| DM1 | Mertansine derivative M4 | Microtubule-depolymerizing[15] |
| DM4 | Mertansine derivative M4 | Microtubule-depolymerizing[15] |
| Duocarmycine | Duocarmycine | DNA-binding agent[13] |
| Calicheamicin | Calicheamicin | DNA minor groove binding agent[13] |
| PBDA | pyrrolibenzodiazepines | DNA-binding agent[13] |
| Doxorubicin | Doxorubicin | Inhibitor of topoisomerase[13] |
| Vinca Alkaloids | Vinca Alkaloids | [13] |
| Metrotrexate | Metrotrexate | [13] |
| Vinblastine | Vinblastine | Microtubule-depolymerizing[13] |
| Daunorubicin | Daunorubicin | [13] |

In some specific embodiments, the therapeutic agent is coupled with said antibody or the functional fragments thereof through a linker. The linker used in the present invention may be linked with the antibody by any ways known in the art, preferably linked through thiol and/or amino. In a particular preferable embodiment, the antibody of the present invention is linked with the linker through thiol. The linker used in the present invention may be a cleavable linker (that is, the linker could be broken in vivo milieu) or an uncleavable linker. In some embodiments, the linker of the present invention is selected from cleavable linkers, preferably from peptide, hydrazone and disulphide linkers, such as maleimidocaproyl-valine-citrulline-p-aminobenzyloxycarbonyl (abbreviated hereafter as mc-vc-pAB or vc). In other embodiments, the linker of the present invention is selected from uncleavable linkers, such as maleimidocaproyl (abbreviated hereafter as mc). In other embodiments, the linker may also be selected from those listed in Table 2 as below.

TABLE 2

List of the available linkers in the conjugates of the present invention

| Abbreviation | Full Name | Type/Action Mechanism |
|---|---|---|
| Mc | Maleimidocaproyl | uncleavable[12] |
| mc-vc-pAB | Maleimidocaproyl valine citrulline p-amino-benzyl | cleavable[12] |
| 3-MPA | 3-maleimido-propionic acid | uncleavable[12] |
| Mal-di-EG-OPFP | Perfluorophenyl 3-(2-(2-(3-(2,5-dioxo-2,5-dihydro-1H-pyrrol-1-yl)propanamido)ethoxy)ethoxy)propanoate | uncleavable[14] |
| Mal-di-EG-OSu | 2,5-dioxopyrrolidin-1-yl 3-(2-(2-(2,5-dioxo-2,5-dihydro-1H-pyrrol-1-yl)ethoxy)ethoxy)propanoate | uncleavable[14] |
| Mal-Tri-EG-OSu | 2,5-dioxopyrrolidin-1-yl 3-(2-(2-(2-(2,5-dioxo-2,5-dihydro-1H-pyrrol-1-yl)ethoxy)ethoxy)ethoxy propanoate | uncleavable[14] |
| Mal-Tetra-EG-OSu | 2,5-dioxopyrrolidin-1-yl 1-(2,5-dioxo-2,5-dihydro-1H-pyrrol-1-yl)-3-oxo-7,10,13,16-tetraoxa-4-azanonadecan-19-oate | uncleavable[14] |
| Br-di-EG-OSu | 2,5-dioxopyrrolidin-1-yl 3-(2-(2-(2-bromoacetamido)ethoxy)ethoxy)propanoate | uncleavable[14] |
| Py-ds-prp-OSu | 2,5-dioxopyrrolidin-1-yl 3-(pyridin-2-yldisulfanyl)propanoate | reducible[14] |
| Py-ds-Prp-OPFP | perfluorophenyl 3-(pyridin-2-yldisulfanyl)propanoate | reducible[14] |
| Py-ds-dmBut-OSu | 2,5-dioxopyrrolidin-1-yl 4-methyl-4-(pyridin-2-yldisulfanyl)pentanoate | reducible[14] |
| Py-ds-dmBut-OPF | perfluorophenyl 4-methyl-4-(pyridin-2-yldisulfanyl)pentanoate | reducible[14] |
| SMCC | N-succinimidyl 4-(maleimidomethyl)cyclohexanecarboxylate | uncleavable[15] |
| MBS | 3-maleimidobenzoic acid N-hydroxysuccinimide ester | uncleavable[13] |
| SATA | S-(N-succinimidyl)thioacetate | uncleavable[13] |
| SPDP | N-succinimidyl 3-(2-pyridyldithio)propionate | reducible[13] |
| SMPT | [(N-succinimidyloxycarbonyl)-1-methyl-1-(2-pyridyldithio)toluene | reducible[13] |

In another aspect, the present invention provides an antibody-drug conjugate having the general formula of Ab-(L-U)n, wherein Ab represents the antibody according to the present invention or the functional fragments thereof, L represents a linker (for example, mc-vc-pAB or mc), U represents the therapeutic agent (preferably, the therapeutic agent is selected from cytotoxic drug, immunopotentiators and radioactive isotopes; more preferably, the therapeutic agent is selected from maytansinoids, dolastatin and derivatives thereof; most preferably, the therapeutic agent is selected from MMAE and MMAF), and n represents an integer from 1 to 8 (for example, 1, 2, 3, 4, 5, 6, 7 or 8). The linker used in the present invention may be a cleavable linker (that is, the linker could be broken in vivo) or an uncleavable linker.

In a further aspect, the present invention provides a pharmaceutical composition, which comprises the antibody according to the present invention or the functional fragments thereof and/or the conjugate according to the present invention, as well as a pharmaceutically acceptable carrier.

In another aspect, the present invention provides a method for treating or preventing cancer (especially HER2-positive cancer), which includes administrating the antibody, polynucleotide, combination of the polynucleotides, expression vector, conjugate and/or pharmaceutical composition according to the present invention in a therapeutically effective amount to a subject in need thereof.

In a further aspect, the present invention provides use of the antibody, polynucleotide, combination of the polynucleotides, expression vector, conjugate and/or pharmaceutical composition according to the present invention in the manufacture of a medicine for treating or preventing cancer.

In a further aspect, the present invention provides the antibody, polynucleotide, combination of the polynucleotides, expression vector, conjugate and/or pharmaceutical composition according to the present invention, which is used for treating or preventing cancer. Preferably, the cancer is HER2-positive cancer. More preferably, the cancer is selected from breast cancer, ovary cancer or gastric cancer. More preferably, the cancer is Lapatinib- and/or Herceptin-resistant cancer, such as Lapatinib- and/or Herceptin-resistant breast cancer, ovary cancer or gastric cancer.

In a further aspect, the present invention provides a hybridoma cell, which was deposited at China General Microbiological Culture Collection Center on Aug. 22, 2013 with the deposit number of 8102 (the date of transfer to Budapest Treaty was Oct. 29, 2013).

In a further aspect, the present invention provides a CHO cell, which was deposited at the China Center for Type Culture Collection on Nov. 6, 2013, with the deposit number of C2013170.

Specifically, the present invention relates to an antibody-drug conjugate (ADC), which can treat cancer. The conjugate comprises a monoclonal antibody which is able to specifically bind to the cancer cell surface receptor, a small molecule drug with cytotoxic effect as well as a linker which can bind the aforementioned two parts together through covalent bond. The present invention also relates to use of these conjugates in the manufacture of a medicine for treating breast cancer and/or ovary cancer and/or gastric cancer.

In some specific embodiments, the present invention relates to an antibody-drug conjugate, which has the general formula of Ab-(L-U)n, wherein Ab represents the monoclonal antibody targeting HER2, L is selected from mc-vc-pAB or mc, U is selected from MMAE or MMAF, and n represents an integer from 1 to 8.

Particularly, the humanized antibody targeting HER2 as disclosed in the present invention is RC48, in which the CDR regions of the heavy chain are as shown by SEQ ID NO. 1, SEQ ID NO. 2 and SEQ ID NO. 3, respectively.

Particularly, the humanized antibody targeting HER2 as disclosed in the present invention is RC48, in which the CDR regions of the light chain are as shown by SEQ ID NO. 4, SEQ ID NO. 5 and SEQ ID NO. 6, respectively.

More particularly, the humanized antibody targeting HER2 as disclosed in the present invention is RC48, which is secreted from the cells deposited at the China Center for Type Culture Collection on Nov. 6, 2013, with the deposit number of C2013170.

Trastuzumab (Herceptin®) is a recombinant humanized monoclonal antibody, selectively targeting on the extracellular domain of human epidermal growth factor receptor-2 (HER2), mainly used for treating HER2-positive cancer. The humanized antibody RC48 of the present invention is a recombinant human HER2 antibody, which is able to bind to the extracellular domain of HER2 with high affinity. In in-vitro experiments and in vivo, RC48 monoclonal antibody shows high ability to inhibit proliferation of HER2-overexpressed human tumor cells.

The two small molecule cytotoxins involved in the present invention are MMAE (Monomethyl auristatin E) or MMAF (Monomethyl auristatin F) (see FIG. 6), which are two kinds of cellular tubulin-inhibiting small molecule. The present invention also relates to two kinds of linkers: Maleimidocaproyl (abbreviated hereafter as mc) and Maleimido-Caproyl-Valine-Citrulline-p-AminoBenzyloxy (abbreviated hereafter as mc-vc-pAB, which is also simply represented by vc in the name of a conjugate) (see FIG. 7); the former linker is uncleavable, while the latter one is cleavable, and the corresponding conjugates show different stability and half-life in vivo. The following three antibody-drug conjugates are formed by RC48 monoclonal antibody linked to the linker through cysteine: RC48-vc-MMAE (see FIG. 8), RC48-vc-MMAF (see FIG. 9) and RC48-mc-MMAF (see FIG. 10).

The conjugate of the present invention has comparable antigen-antibody binding capacity in vitro with RC48 naked antibody, and T-DM1. In the cell viability assay, its cytotoxicity is significantly higher than that of RC48 naked antibody, Herceptin, T-DM1, in which the cells used in the experiment include high HER2-expressed breast cancer cell strain SK-BR-3 (FIG. 12) and high HER2-expressed ovary cancer cell strain SK-OV-3 (FIG. 13). In the animal experiments of nude mice transplantation tumor model, the conjugate of the present invention has significant antitumor effect to BT474 human breast cancer tumor-bearing nude mouse (FIG. 14), and the preferable conjugate shows significant antitumor activity to Herceptin®- and Lapatinib-resistant tumor-bearing nude mouse, with the effect significantly better than positive control drugs (FIG. 15); meanwhile, the antibody conjugate of the present invention shows unexpectedly antitumor effect to ovary cancer and gastric cancer transplantation tumor-bearing nude mouse (FIG. 16 and FIG. 17). Through the in vivo mouse experiment, it is determined that the maximum tolerance doses of the present conjugate are as follows: RC48-mc-MMAF: >150 mg/kg, RC48-vc-MMAF: 60 mg/kg, RC48-vc-MMAE: 100 mg/kg, respectively. Further, the efficacy test is carried out by using human ovary cancer transplantation tumor model of nude mice, and it is found that, during the administration of the drug, by observing the changing of the volumes of the mice tumor model and the body weights of the mice per se, the potency of the conjugate is significantly higher than those of naked antibody and T-DM1. Furthermore, the body weights of the mice are increased (FIG. 18), showing a good potency with low toxic and high efficiency. The conjugate provides a new candidate drug choice for treating HER2-positive cancer, HER2 antibody drug resistant cancer, tyrosine kinase inhibitor resistant cancer and other relevant diseases.

In some specific embodiments, the antibody according to the present invention or the functional fragments thereof is isolated.

In some specific embodiments, the antibody according to the present invention or the functional fragments thereof is monoclonal antibody.

In some specific embodiments, the antibody according to the present invention or the functional fragments thereof is humanized antibody.

In some specific embodiments, the antibody according to the present invention or the functional fragments thereof has ADCC activity.

In some specific embodiments, the antibody according to the present invention or the functional fragments thereof has CDC activity.

In some specific embodiments, the antibody according to the present invention or the functional fragments thereof specifically binds to HER2, while basically not binding to EGFR, HER3 and HER4.

In some specific embodiments, the antibody according to the present invention or the functional fragments thereof is IgG1K antibody.

In some specific embodiments, the antibody according to the present invention or the functional fragments thereof is useful for treating or preventing cancer, in which the cancer over-expresses HER2.

DESCRIPTION OF THE SPECIFIC EMBODIMENTS

Definitions

Figure 1:
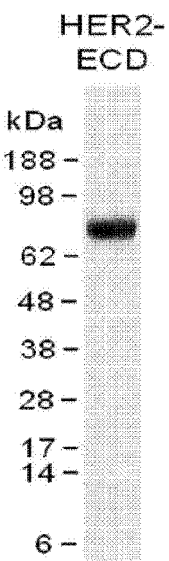
FIG. 1 represents SDS-PAGE figure of the purified human recombinant protein HER2-ECD, which is stained with Coomassie Brilliant Blue. Each well is loaded with 10 μg.

Unless otherwise defined, all of the technological terms used herein have the same meanings as understood by those skilled in the art. As to the definitions and terms in the art, the skilled person may refer to Current Protocols in Molecular Biology (Ausubel) for more details. The abbreviation of the amino acid residue is the standard three-letter and/or one-letter code used in the art, which represents one of the 20 common L-amino acids.

Although the present invention uses the number range and parameter approximate value in broad sense, the number as shown in a specific example is recited as exactly as possible. However, any number itself includes inevitably error to some extent, which is caused by the standard deviation produced from each of their measurements. Furthermore, all of the ranges as disclosed in the present invention should be understood to cover any and all of the sub-ranges contained therein. For example, the range of "from 1 to 10" as recited should be considered as containing any and all of the sub-ranges between the minimal value of 1 and the maximal value of 10 (including the end points); that is, all of the sub-ranges start from the minimal value of 1 or from another greater point (such as from 1 to 6.1), and the sub-ranges end with the maximal value of 10 or another smaller point (such as from 5.5 to 10). Moreover, any of the reference recited as "incorporated herein" should be understood as being incorporated in its entirety.

Furthermore, it should be noted that, as used in the present specification, the singular form includes the plural form of the indicated subject, unless it is clearly and definitely limited to one indicated subject. The term "or" may be interchangeably used with "and/or", unless it is clearly indicated in the context.

The term "pharmaceutical composition", "combination drug" and "drug combination" as used herein may be used interchangeably, which means the combination for achieving a certain specific purpose by combining at least one kind of drugs and optionally pharmaceutically acceptable carrier or adjuvant together. In some embodiments, the pharmaceutical composition includes the combination separated in time- and/or spatial-level, as long as it can achieve the purpose of the present invention by working together. For example, the ingredients contained in the pharmaceutical composition (such as the antibody, nucleic acid molecule, nucleic acid molecule combination and/or conjugate) can be administrated to a subject entirely or separately. When the ingredients contained in the pharmaceutical composition are separately administrated to the subject, the ingredients can be administrated simultaneously or sequentially. Preferably, the pharmaceutically acceptable carrier is water, buffered aqueous solution, isotonic saline solution such as PBS (phosphate buffer solution), glucose, mannitol, dextrose, lactose, starch, magnesium stearate, cellulose, magnesium carbonate, 0.3% of glycerine, hyaluronic acid, ethanol or polyalkylene glycol such as poly(propylene glycol), triglyceride and the like. The types of used pharmaceutically acceptable carriers especially rely on whether the composition according to the present invention is formulated for oral, nasal, intracutaneous, subcutaneous, intramuscular or intravenous administration. The composition according to the present invention may comprise wetter, emulsifier or buffer materials as additive.

The composition, vaccine or pharmaceutical formulation according to the present invention could be administrated by any suitable routes, such as oral, nasal, intracutaneous, subcutaneous, intramuscular or intravenous administration.

The term "therapeutic agent" as used herein means any material or entity which can play a role in treating (for example, treating, preventing, alleviating or inhibiting any diseases and/or conditions), including but not limited to: chemical therapeutic agent, radioactive therapeutic agent, immune therapeutic agent, thermally therapeutic agent and the like.

"CDR region" or "CDR" as used herein means the hypervariable region of the heavy chain and light chain of the immunoglobulin, as defined by Kabat et al., (Kabat et al., Sequences of proteins of immunological interest, 5th Ed., U.S. Department of Health and Human Services, NIH, 1991 and the subsequent versions). There are three CDRs of the heavy chain and three CDRs of the light chain. Depending on the situations, the term "CDR" or "CDRs" as used herein is meant to refer to one of or a few of or even all of these regions which contain most of the amino acid residues that are responsible for binding through the affinity of the antibody directed to the antigen or its recognition epitope.

By the "uniformity", "identity" or "similarity" between two nucleic acid or amino acid sequences in the present invention, it means a percentage of identical nucleotides or amino acid residues between the two sequences to be compared, obtained after the best alignment (optimal alignment). This percentage is purely statistical, and the differences between the two sequences are randomly distributed and cover their full length. A sequence comparison between two nucleic acid or amino acid sequences is usually performed by comparing these sequences after their optimal match. Said comparison could be performed through a segment or a "comparison window". In addition to being performed manually, the optimal alignment for sequence comparison can be performed by means of the local homology algorithm of Smith and Waterman (1981) (Ad. App. Math. 2:482), by means of the local homology algorithm of Neddleman and Wunsch (1970) (J. Mol. Biol. 48:443), by means of the similarity search method of Pearson and Lipman (1988) (Proc. Natl. Acad. Sci. USA 85:2444) and by means of computer softwares using these algorithms (GAP, BESTFIT, FASTA and TFASTA in the Wisconsin Genetics Software Package, Genetics Computer Group, 575 Science Dr., Madison, Wis., or by using BLAST N or BLAST P comparison software).

A "therapeutically effective amount" or "effective amount" as used herein refers to a dose sufficient to show the benefits directed to the subject being administered. The actual dose as well as the rate and time course of the administration will vary depending on the self-condition and the level of severity of the subject being treated. The treatment prescription (such as the determination on the dose, etc.) is finally the responsibility of the general practitioner and other doctors, and the determination is made based on above factors. Usually, the determination is made in consideration of the disease being treated, the individual condition of the patient, delivery site, method of administration and any other factors known by the doctors.

The term "subject" as used herein means mammals such as human being, and also may be other animals, such as wild animals (such as hern, stork, crane, etc.), livestocks (such as duck, goose, etc.) or laboratory animals (such as chimpanzee, monkey, rat, mouse, rabbit, guinea pig, woodchuck, ground squirrel, etc.).

The term "antibody" means the intact antibody and any antigen-binding fragments thereof ("antigen-binding portion") or single chain. The "full-length antibody" means a protein comprising at least two heavy (H) chains and two light (L) chains inter-linked by disulfide bonds. Each heavy chain contains one heavy chain variable region (abbreviated as VH) and one heavy chain constant region. The heavy chain constant region contains three domains, CH1, CH2 and CH3. Each light chain contains one light chain variable region (abbreviated as VL) and one light chain constant region. The light chain constant region contains one domain, CL. The VH and VL regions can be further subdivided into various regions with hypervariability, termed complementarity determining region (CDR), interspersed with various regions that are more conserved, termed framework region (FR). Each VH and VL is composed of three CDRs and four FRs, arranged from amino-terminus to carboxy-terminus in the following order: FR1, CDR1, FR2, CDR2, FR3, CDR3, FR4. These variable regions of the heavy chains and light chains comprise a binding domain for interacting with an antigen. The constant region of the antibodies may mediate the binding of the immunoglobulin to host tissues or factors, including various cells of the immune system (such as effector cells) and the first component of the classical complement system (Clq). Chimeric or humanized antibody is also encompassed in the antibody according to the present invention.

The term "humanized antibody" refers to an antibody comprising the CDR region from a non-human-derived antibody, and the other portions of this antibody molecule are from one (or a few) type(s) of human antibody. Moreover, for the purpose of retaining binding affinity, some residues in the framework region (FR) segment can be modified (Jones et al., Nature 321:522-525, 1986; Verhoeyen et al., Science, 239:1534-1536, 1988; Riechmann et al., Nature 332:323-327, 1988). The humanized antibody or the fragments thereof according to the present invention may be prepared by means of those technologies as known by those skilled in the art (such as those described in the following documents: Singer et al., J. Immun. 150:2844-2857, 1992; Mountain et al., Biotechnol. Genet. Eng. Rev., 10:1-142, 1992; or Bebbington et al., Bio/Technology, 10:169-175, 1992).

The term "chimeric antibody" refers to an antibody, in which the sequence of the variable region is from one species while the sequence of the constant region is from another species; for example, the sequence of the variable region is from mouse antibody while the sequence of the constant region is from human antibody. The chimeric antibody or fragments thereof according to the present invention may be prepared by using a gene recombinant technology. For example, the chimeric antibody may be produced by cloning recombinant DNA which comprises a promoter and a sequence encoding the variable region of the non-human (especially murine) monoclonal antibody according to the present invention and a sequence encoding the constant region of human antibody. The chimeric antibody of the present invention encoded by this recombinant gene will be, for example, murine-human chimera, which has the specificity determined by the variable region derived from murine DNA and has the isotype thereof determined by the constant region derived from human DNA. For the method of preparing the chimeric antibody, references could be made by, for example, Verhoeyn et al. (BioEssays, 8:74, 1988).

The term "monoclonal antibody" means an antibody molecular preparation with single molecular constitution. The monoclonal antibody composition shows a single binding specificity and affinity directed to a specific epitope.

The term "mRC48 antibody" as used herein means, unless otherwise indicated, anti-HER2 murine-derived monoclonal antibody mRC48 obtained by the inventor. The term "RC48 antibody" as used herein means, unless otherwise indicated, humanized anti-HER2 antibody RC48, which is derived from mRC48 antibody by humanized engineering.

The cRC48 antibody as used herein means chimeric RC48 antibody, i.e., human-murine chimeric antibody, which contains murine-derived variable region and human-derived constant region. The difference between cRC48 antibody and RC48 antibody only lies in the difference of the framework region in the variable region, that is, the framework region of cRC48 is murine-derived, while the framework region of RC48 is human-derived.

The term "functional fragment" as used herein particularly means the antibody fragment, such as Fv, scFv (sc indicates single chain), Fab, F(ab')2, Fab', scFv-Fc fragments or diabody, or any fragments which can increase half-life by means of chemical modification or by being incorporated into liposome. Said chemical modification includes, for example, adding poly(alkylene) glycol such as polyethylene glycol ("pegylated") (called Fv-PEG, scFv-PEG, Fab-PEG, F(ab')2-PEG or Fab'-PEG pegylated fragments, "PEG" indicates polyethylene glycol), and said fragments have EGFR-binding activity. Preferably, the functional fragment is composed of or comprises partial sequences from the heavy or light variable chains of the antibody derived therefrom, the partial sequence is sufficient to retain the same binding specificity and sufficient affinity as the antibody derived therefrom (for EGFR, preferably at least equals to $1/100$ of the affinity of the antibody derived therefrom, more preferably at least equals to $1/10$). This functional fragment will contain at least 5 amino acids, preferably 10, 15, 25, 50 and 100 continuous amino acids of the antibody sequence derived therefrom.

Typically, for the purpose of preparing monoclonal antibody or functional fragments thereof, especially murine-derived monoclonal antibody or functional fragments thereof, reference may be made by the technologies particularly described in the manual "Antibodies" (Harlow and Lane, Antibodies: A Laboratory Manual, Cold Spring Harbor Laboratory, Cold Spring Harbor N.Y., pp. 726, 1988), or by the technologies for preparing from the hybridoma cells as described by Kohler and Milstein (Nature, 256:495-497, 1975).

The monoclonal antibody according to the present invention may be for example purified on the affinity column which has already been fixed with HER2 antigen (e.g., HER2-ECD) or one of the fragments containing the epitope which can be specifically recognized by the monoclonal antibody according to the invention in advance. More specifically, the monoclonal antibody may be purified as follows: by Protein A and/or G chromatography, followed by or not followed by ion exchange chromatography which is aimed to eliminate residual protein contaminants as well as DNA and LPS, followed by or not followed by the exclusion chromatography on the Sepharose gel which is aimed to eliminate the potential aggregates caused by the dimers or other polymers. In a more preferable way, all of these technologies may be used simultaneously or continuously.

The term "dolastatin" as used herein means a polypeptide separated from a kind of marine organism *Dollabella auricularia*, which includes but not limited to dolastatin 10 and dolastatin 15. The dolastatin is an inhibitor of mitosis, showing a strong anticancer activity, and thus is regarded as a candidate of the anticancer drug. The researchers further discover and synthesize many derivatives of dolastatin, such as MMAE and MMAF.

The term "linker" as used herein means the part which links the antibody with the drug in the antibody-drug conjugate (i.e. ADC), which could be cleavable or uncleavable. The cleavable linker (i.e., breakable linker or biodegradable linker) may be broken in or on the target cells, and thereby releasing the drug. In some embodiments, the linker of the present invention has very good stability and greatly decreases the release of the drug during the process of delivering to the target (e.g., in blood), thereby reducing the side effect and toxicity. In some particular embodiments, the linker of the present invention is selected from cleavable linker, such as the linker based on disulphide (which is selectively broken in the tumor cells at a higher thiol concentration), peptide linker (which is cleaved by the enzyme in the tumor cells), and hydrazone linker. In further particular embodiments, the linker of the present invention is selected from uncleavable linker, such as thio ether linker. Preferably, the linker of the present invention is selected from cleavable mc-vc-pAB linker and uncleavable mc linker.

The following examples are provided to demonstrate and further explain some preferable embodiments and aspects of the present invention, and should not be explained to limit its scopes.

Example 1 Preparation and Sequence Analysis of the Murine-Derived Monoclonal Antibody mRC48

1) Expression and Purification of HER2 Antigen

Firstly, in the present study, recombinant human HER2 protein HER2-ECD composing of its extracellular domain (ECD) was prepared and utilized as the antigen for following immunization and monoclonal antibody generation as well as various biological assays.

The cDNA fragment encoding HER2-ECD (amino acids Thr23 to Thr652, GenBank accession M11730) was cloned into pcDNA3 expression vector (Invitrogen Inc.) by PCR.

The detailed method comprised: obtaining cDNA of HER2-ECD coding region from HER2$^+$ SKBR3 cell strain (ATCC NO. HTB-30) by means of RT-PCR method (the kit of ImProm-II™ Reverse Transcription System from Promega Inc. was applied). The primers were:

P1:
(SEQ ID NO: 7)
5'CG<u>GGATCC</u>TGCCACCAGCTGTGCGCC,

P2:
(SEQ ID NO: 8)
5'GC<u>TCTAGA</u> TCAGTTGATGGGGCAAGGCT;

the underlined sequences were introduced BamHI, XbaI enzyme sites respectively. PCR amplification was run with the template of cDNA of reverse transcribed HER2-ECD by using the aforementioned primers, with the amplification conditions comprising 30 cycles of denaturing at 94° C. for 30 s, annealing at 60° C. for 30 s, extending at 72° C. for 1 min, finally extending at 72° C. for 10 min. Then, the PCR fragments were recovered, digested with BamHI and XbaI enzymes (NEB), and linked with pcDNA3 vector. The C-terminal of HER2-ECD was added a polyhistidine tag for purification conveniently. HEK293 cells (US ATCC) were transfected with the constructed DNA expression vector, and the soluble protein HER2-ECD with His-tag was purified from the cell culture fluid by Ni-NTA affinity chromatography (Qiagen). SDS-PAGE and Coomassie Brilliant Blue staining indicated that the purified HER2-ECD proteins had a homogenicity greater than 95%, and the result was shown in FIG. 1. The soluble HER2-ECD was in the form of monomer, with the relative molecular weight of ~75 kDa which was slightly greater than the calculated molecular weight (71 kDa), suggesting that the protein was glycosylated in HEK293 cells. The resulting purified HER2-ECD protein was further concentrated, and transferred into the sterile PBS buffer (pH7.4), for subsequent in vivo and in vitro analysis.

2) Production and Screen of Hybridoma Cells

HER2-ECD as described above was used as the antigen for immunizing the mouse and monoclonal antibody generation. Immunization, hybridoma cells fusion and primary screen were conducted according to standard procedures (reference: WHO Technical Report Series, No. 822, 1992 Annex 3). Four Balb/c mice (commercially obtained from Shanghai Slac Laboratory Animal Co. Ltd.) were immunized with equal volume of well-blended 0.25 ml HER2-ECD protein (50-100 µg) and 0.25 ml Freund's complete adjuvant (Difco Lab). Two weeks later, the second injection was carried out with Freund's incomplete adjuvant (Difco Lab) in which the amount of antigen was 25-50 µg/0.5 ml/mouse. Three weeks later, the third injection was carried out in which the amount was the same with that in the second injection. Ten days after the third injection the blood was drawn. The mice serum were detected by enzyme-linked immunosorbent assay (ELISA), and the spleens of the two mice with highest anti-HER2 antibody titer in serum were taken, which were then fused with the myeloma cell P3X63Ag8 (ATCC CRL-1580). The fused cells were diluted onto ten 96-well plates, and the preliminary screen was carried out through ELISA method depending on the binding capacity with HER2-ECD. In a classical ELISA assay, the Nunc Maxisord 96-well plate was coated with HER2-ECD (0.2-1 µg/ml), and then incubated with gradient diluted mouse serum or hybridoma supernatant (100 µL). Murine-derived anti-HER2 antibody was detected by the goat F(ab')2 anti-murine IgG Fc specific second antibody coupled with horse radish peroxidase (Invitrogen Inc.).

The supernatants of 400 hybridoma cell strains were screened by means of ELISA method, 36 of which showed a strong HER2-ECD binding capacity. Ten strains of hybridoma cells with the strongest HER2 binding capacity were chosen, and the subclone hybridoma cell strains were screened through limited dilution method. The binding affinity of the subclone hybridoma cell strains with HER2 was determined by suspension culture of the subclone hybridoma cell strains, protein purification and ELISA, and the binding capacity of the subclone hybridoma cell stains with HER2 expressed naturally on the surface of the human breast cancer cell strains was further examined by flow cytometer (BD FACS Calibur) (see Example 4 for more detailed descriptions). Finally, a hybridoma cell strain mRC48 (murine-derived IgG1k) was determined through sequence analysis, which possessed a strong HER2 binding capacity, and then it was further analyzed through ELISA and cell experiments. The hybridoma cell mRC48 was deposited at the China General Microbiological Culture Collection Center on Aug. 22, 2013, with the deposit number of 8102 (the date of transfer to Budapest Treaty was Oct. 29, 2013).

3) Sequence Analysis of the Anti-HER2 Hybridoma Cell Clone mRC48

The variable regions of the heavy and light chains of the hybridoma cell clone mRC48 were sequenced by 5'-end rapid amplification using commercially available kit SMART™ RACE cDNA Amplification Kit (Clontech Inc.) according to instruction.

The total RNA was extracted from the hybridoma cells by RNApure Tissue Kit (Beijing Kangweishiji Biological Technology Co. Ltd.), and the reverse transcription of the total RNA was carried out by SMART™ RACE cDNA Amplification Kit, using the total RNA as the template, using the primers in the kit, adding the reverse transcriptase SMART-Scribe™ Reverse Transcriptase and obtaining RACE-Ready first chain cDNA through reverse transcription according to the steps as provided by the kit, and then running two rounds of PCR in which: the first round of PCR was carried out by using the obtained cDNA as the template, UPM provided in the kit as 5'-end primer, and mRC48-VL-1/mRC48-VH-1 as 3'-end primer. The PCR reaction conditions included pre-denaturing at 94° C. for 5 min, 25 cycles of amplification (denaturing at 94° C. for 30 s, annealing at 68° C. for 30 s, extending at 72° C. for 2 min), finally extending at 72° C. for 10 min.

The second round of PCR was carried out by using the product of the first round of PCR as the template, NUP provided in the kit as 5'-end primer, and mRC48-VL-2/mRC48-VH-2 as 3'-end primer. The PCR reaction conditions included: pre-denaturing at 94° C. for 5 min, 25 cycles of amplification (denaturing at 94° C. for 30 s, annealing at 68° C. for 30 s, extending at 72° C. for 2 min), finally extending at 72° C. for 10 min. In this way, the variable regions of the heavy and light chains of the above hybridoma cell clone mRC48 were obtained.

| Primer | Primer Sequence |
| --- | --- |
| mRC48-VL-1 | GTTGGTGCAGCATCAGCCCGTT (SEQ ID NO: 9) |
| mRC48-VL-2 | GTTCACTGCCATCAATCTTCCAC (SEQ ID NO: 10) |
| mRC48-VH-1 | GCCAGTGGATAGACAGATGG (SEQ ID NO: 11) |
| mRC48-VH-2 | AGGTCACTGTCACTGGCTCAG (SEQ ID NO: 12) |

The PCR products were purified by agarose gel electrophoresis, and subcloned into pCR2.1TOPO clone vector (Invitrogen Inc.). By PCR, DNA from 10 independent cloned plasmids were obtained, and further sequenced by using M13 forward and reverse primers. The DNA sequence analysis indicated that, all of these 10 clones possessed cDNA encoding the same VH or VL polypeptide. The amino acid sequence of the complementarity determining region (CDR) was defined by Kabat Code, and listed in Table 3. The sequence comparison analysis indicated that, the CDR of anti-HER2 mRC48 is significantly different from those of known HER2 antibodies including Herceptin (Trastuzumab).

TABLE 3

The amino acid sequences of the CDRs of anti-HER2 monoclonal antibody mRC48

|  | Heavy chain (VH) | Light chain (VL) |
| --- | --- | --- |
| CDR1 | DYYIH (SEQ ID NO. 1) | KASQDVGTAVA (SEQ ID NO. 4) |
| CDR2 | RVNPDHGDSYYNQK FKD (SEQ ID NO. 2) | WASIRHT (SEQ ID NO. 5) |
| CDR3 | ARNYLFDHW (SEQ ID NO. 3) | HQFATYT (SEQ ID NO. 6) |

Example 2 Humanization of Anti-HER2 Monoclonal Antibody mRC48

We humanized murine monoclonal anti-HER2 antibody mRC48 by grafting its light chain or heavy chain CDRs into a human IgG1κ framework region.

According to the published methods, we know that human IgG1κ was highly homologous to murine RC48 antibody (mRC48). Thereby, we designed a light chain variable region of humanized RC48 antibody (RC48-VL), and a heavy chain variable region of humanized RC48 antibody (RC48-VH), combining them to a humanized anti-HER2 antibody: RC48. The overall sequence of RC48-VH had a similarity of 84% with human IgG1 VH gene. RC48 antibody contained the light chain variable region RC48-VL and the heavy chain variable region RC48-VH.

Humanized anti-HER2 monoclonal antibody RC48 was obtained by the method of CDR transplantation, in which the heavy or light chain variable region was synthesized directly by GenScript (Nanjing) Co. Ltd., and the synthesized variable region contained Kozak consensus sequence, initiation codon, heavy or light chain signal peptide, human-derived framework region and murine-derived CDR, which was linked with human IgG1κ constant region to form a complete fragment through the method of overlap extension PCR.

The primers of overlap extension PCR included:

Heavy chain:
VH1:
(SEQ ID NO: 13)
5'CGCGGATCC GCCGCCACCATGGGATGGAGCT3'

VH2:
(SEQ ID NO: 14)
5'GATGGGCCCTTGGTGCTAGCGGAGCTCACTGTCACCAGTGTT3'

CH1:
(SEQ ID NO: 15)
5'GCTAGCACCAAGGGCCCATC3'

CH2:
(SEQ ID NO: 16)
5'CCGGAATTCTTTACCGGGAGACAGGGAGA3'

Light chain:
VL1:
(SEQ ID NO: 17)
5'CGCGGATCC GCCGCCACCATGGACATGAGGGT3'

VL2:
(SEQ ID NO: 18)
5'GATGGTGCAGCCACAGTACGCTTTATCTCAACTTTTG TAC3'

CL1:
(SEQ ID NO: 19)
5'CGTACTGTGGCTGCACCAT3'

CL2:
(SEQ ID NO: 20)
5'CCGGAATTCACACTCTCCCCTGTTGAAGC3'.

The amplification of heavy chain was carried out as follows: firstly used the synthesized variable region as template and VH1 and VH2 as primers for amplifying the variable region of heavy chain; used human IgG1κ heavy chain constant region as template and CH1 and CH2 as primers for amplifying the constant region of heavy chain. The amplification conditions included 30 cycles of denaturing at 94° C. for 30 s, annealing at 60° C. for 30 s, extending at 72° C. for 1 min, finally extending at 72° C. for 10 min. Then, the heavy chain sequence of RC48 was amplified by using the two PCR products as template and VH1 and CH2 as primers. The amplification conditions included 30 cycles of denaturing at 94° C. for 30 s, annealing at 60° C. for 30 s, extending at 72° C. for 2 min, finally extending at 72° C. for 10 min.

The amplification of light chain was carried out as follows: firstly used the synthesized variable region as template and VL1 and VL2 as primers for amplifying the variable region of light chain; used human IgG1κ light chain constant region as template and CL1 and CL2 as primers for amplifying the constant region of light chain. The amplification conditions included 30 cycles of denaturing at 94° C. for 30 s, annealing at 60° C. for 30 s, extending at 72° C. for 1 min, finally extending at 72° C. for 10 min. Then, the light chain sequence was amplified by using the two PCR products as template and VL1 and CL2 as primers. The amplification conditions included 30 cycles of denaturing at 94° C. for 30 s, annealing at 60° C. for 30 s, extending at 72° C. for 2 min, finally extending at 72° C. for 10 min.

Therefore, we obtained a humanized anti-HER2 monoclonal antibody RC48, in which RC48 contained human IgG1κ heavy chain constant region and heavy chain variable region RC48-VH, and human IgG1κ light chain constant region and light chain variable region RC48-VL.

Human-murine chimeric antibody cRC48 was also obtained by the same methods, in which the murine variable region was linked with human IgG1κ constant region to form a complete fragment through overlap extension PCR.

Figure 2:
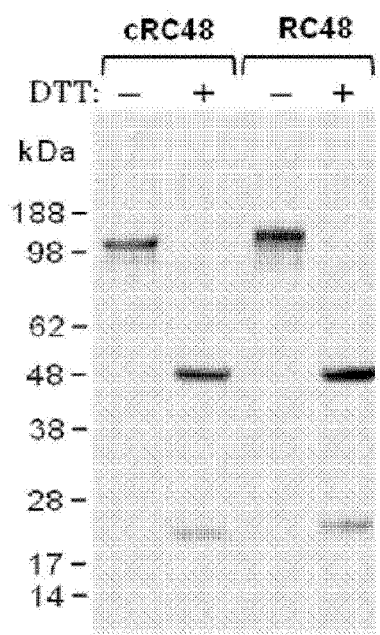
FIG. 2 represents SDS-PAGE analysis figures of cRC48, RC48, in which each well is loaded with 2 μg antibody.

Each of the amplified fragments was subcloned into the expression vector pcDNA3.0 respectively. The different constructed plasmids were transfected into suspended CHO cells (Invitrogen), for generating different recombinant antibodies, the purification was carried out by Protein A and the subsequent characteristic analyses were performed. The chimeric anti-HER2 RC48 (called cRC48) was consisted of a murine-human chimeric cRC48 heavy chain and a light chain. RC48 comprises humanized heavy chain RC48-VH and humanized light chain RC48-VL. cRC48 and RC48 were both able to be expressed, and the antibodies were collected from the CHO cell supernatant, purified by Protein A, and analyzed by SDS-PAGE assay under reductive and non-reductive conditions (see FIG. 2). The aforementioned CHO cells secreting RC48 antibody (that is, the CHO cells transfected with human IgG1κ heavy chain constant region and heavy chain variable region RC48-VH, and human IgG1κ light chain constant region and light chain variable region RC48-VL) were deposited at the China Center for Type Culture Collection on Nov. 6, 2013 with the deposit number of C2013170.

Example 3 Characterization Analysis of Anti-HER2 RC48 Antibody

Figure 3:
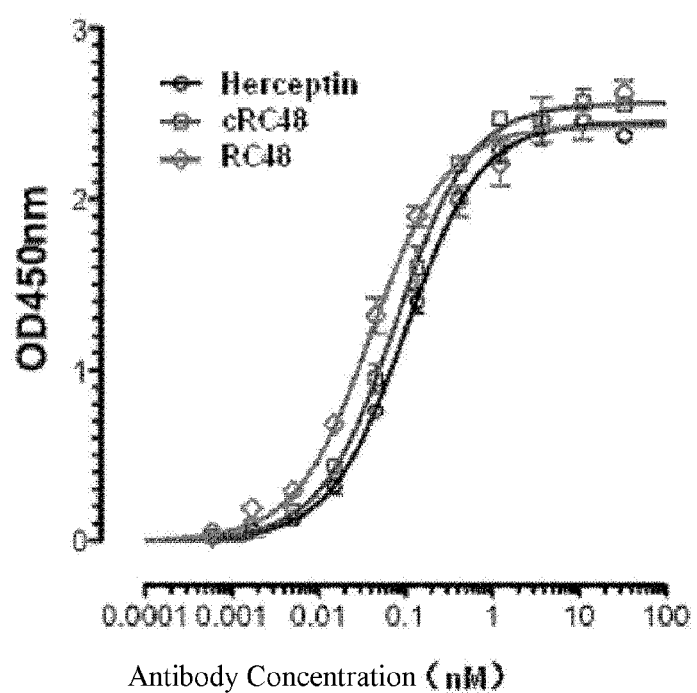
FIG. 3 shows the binding affinity between humanized antibody RC48 and HER2-ECD determined by ELISA assay, and the calculated binding affinity constant Kd. Herceptin and cRC48 are used as control in this assay.

The HER2-binding affinity constants (Kd) of chimeric cRC48 and humanized RC48 antibody (RC48) were determined by ELISA method, and the detailed method could be found in Example 1, that is, the 96-well plate was coated with soluble HER2-ECD protein, then incubated with diluted antibodies (Herceptin and chimeric cRC48 as controls), and the HER2-ECD relevant antibodies (all of the forms of human IgG1κ) were detected by the HRP-coupled goat F(ab')2 anti-human IgG Fc specific second antibody (invitrogen). The binding curve was plotted, and the surface binding affinity constant (Kd) value was further calculated for each anti-HER2 antibody by single site specific binding non-linear equation (Journal of Immunological Methods, 270:155-162, 2002) (FIG. 3 showed a typical HER2-binding curve obtained from 3 independent ELISA assays). The results of ELISA assay are shown in FIG. 3.

As known by the 3 independent assays, compared with cRC48 (average affinity constant of 77 pM) and Herceptin (average affinity constant of 97 pM), humanized anti-HER2 antibody RC48 had higher HER2-ECD binding affinity, with the average affinity constant of 44 pM. The result is shown in Table 4.

TABLE 4

Comparison of the average affinity constant between the antibody of the present invention and Herceptin

| Sample | Average affinity constant |
|---|---|
| Herceptin | 97 pM |
| cRC48 | 77 pM |
| RC48 | 44 pM |

Example 4 Binding Capacity of Humanized Antibody RC48 with HER2

1) Binding Affinity Experiments of RC48 Antibody with HER2

Figure 4:
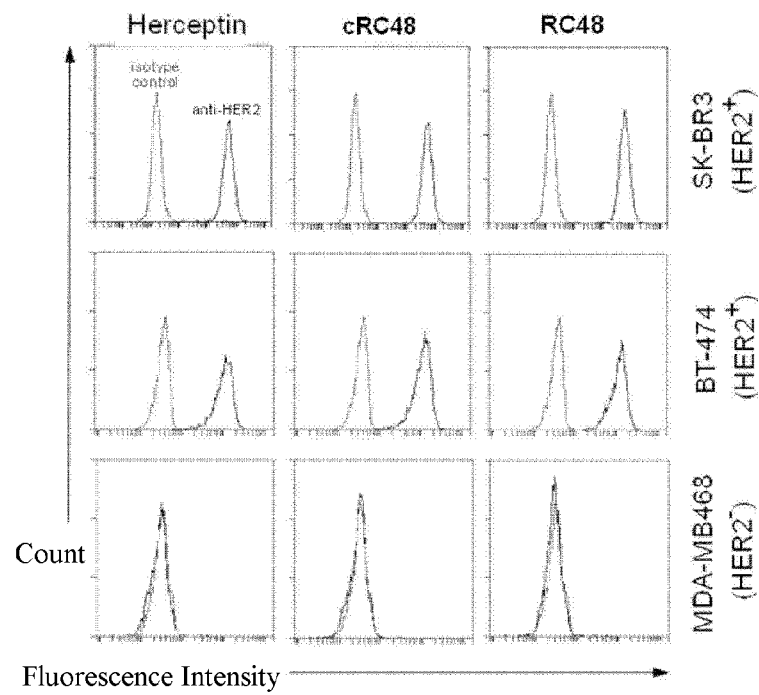
FIG. 4A represents the analysis of binding capacity of anti-HER2 humanized antibody RC48 with HER2+ cells (SK-BR3, BT474) and HER2− cells (MDA-MB468) by flow cytometry.
FIG. 4B shows the analysis of binding capacity of anti-HER2 antibody with BT474 cellular surface antigen by flow cytometry at different antibody concentrations. The anti-HER2 antibody includes Herceptin, cRC48, RC48. A total of 5×10$^4$ cells are analyzed.
Figure 4:
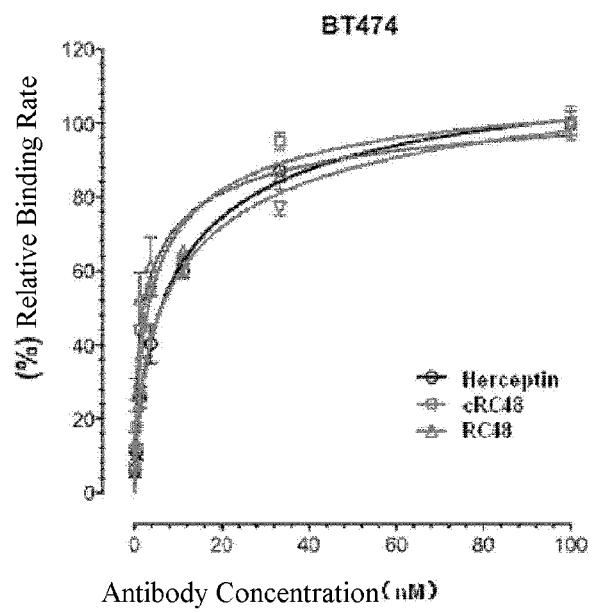

The binding capacity of humanized anti-HER2 antibody RC48 with HER2 which was endogenously expressed in human breast cancer cells was detected by flow cytometer, and the result was shown in FIG. 3. 6 µg of human IgG (control group), Herceptin, cRC48, RC48 were co-incubated with two kinds of HER2+ cell line human breast cancer cell SK-BR-3, BT474 and HER2+ cell MDA-MBA468 ($2 \times 10^7$ cells) on ice for 30-45 minutes, respectively. After 2 times of thoroughly washing with 4 ml cold PBS, the antibodies binding with the cell surface were detected by R-PE-coupled goat anti-human IgG Fc specific second antibody (15 µl, 25 µg/mL), and then analyzed by flow cytometer (BD FACSCalibur). No binding was detected between the human IgG1 (control group) and the three kinds of cancer cells. In contrast, there was a strong binding between Herceptin, cRC48, RC48 with the two kinds of HER2 positive cells, while no binding with HER2 negative cells, suggesting that this binding was HER2 specific (as shown in FIG. 4a). By comparing the average fluorescence intensity of the isotype control group, it was found that compared with Herceptin and cRC48, RC48 showed a higher binding affinity. By titering the concentration of anti-HER2 antibody and analyzing the cell numbers in flow cytometry, a cell-based binding curve of anti-HER2 antibody with HER2 on cell surface was obtained, and the result was shown in FIG. 4b. Humanized anti-HER2 antibody RC48 showed a significant binding affinity, which had the binding affinity (Kd) with HER2 on BT474 cell surface of 4 nM, while the binding affinities for Herceptin and cRC48 were 10 nM and 5 nM respectively, and the results were shown in Table 5.

TABLE 5

Binding affinity of the antibody of the present invention with HER2 on BT474 cell surface

| Sample | Binding affinity Kd |
|---|---|
| Herceptin | 10 nM |
| cRC48 | 5 nM |
| RC48 | 4 nM |

2) Antigen Binding Specificity Experiment

Figure 5:
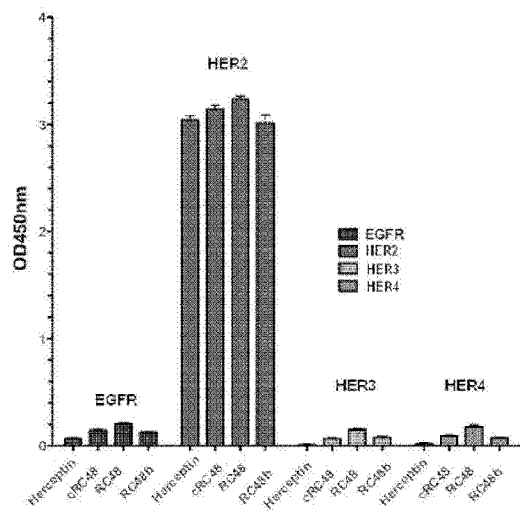
FIG. 5 indicates that RC48 only shows specific binding affinity with HER2, but not with EGFR, HER3 and HER4.
Figure 6:
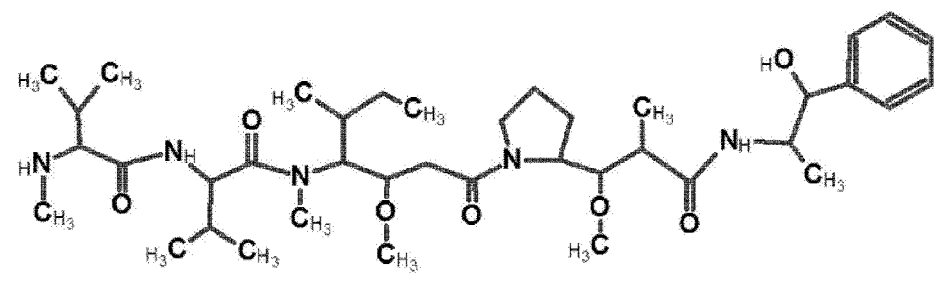
FIG. 6 shows the molecular structures of antitubulin, MMAE and MMAF.
Figure 6:
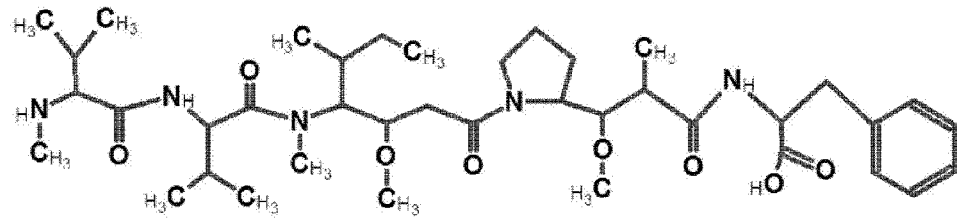
Figure 7:
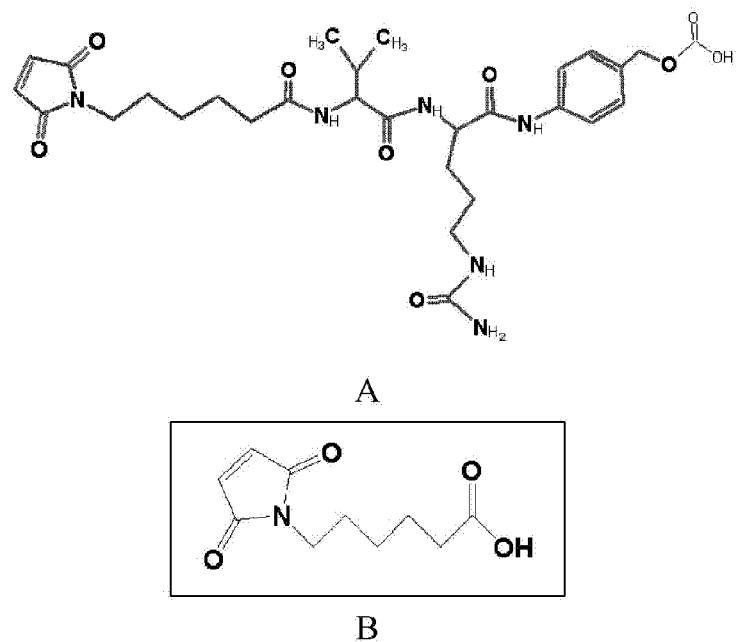
FIG. 7 shows the molecular structures of chemical linkers, mc-vc-pAB and mc.
Figure 8:
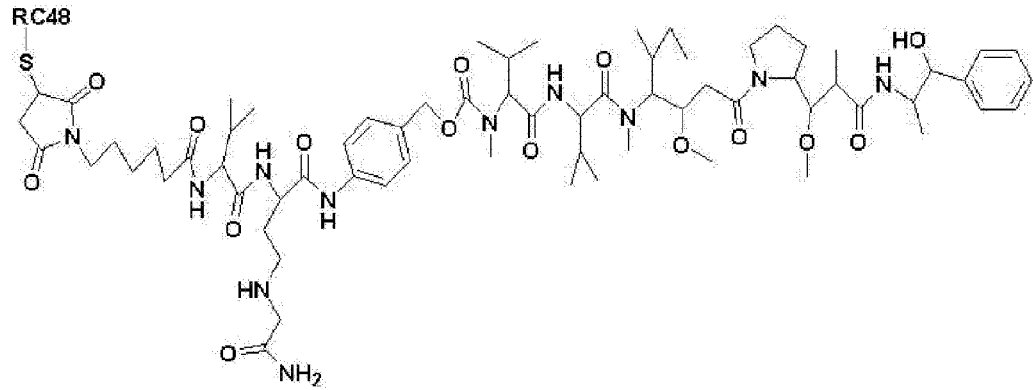
FIG. 8 shows the molecular structure of RC48 antibody-drug conjugate (RC48-vc-MMAE).
Figure 9:
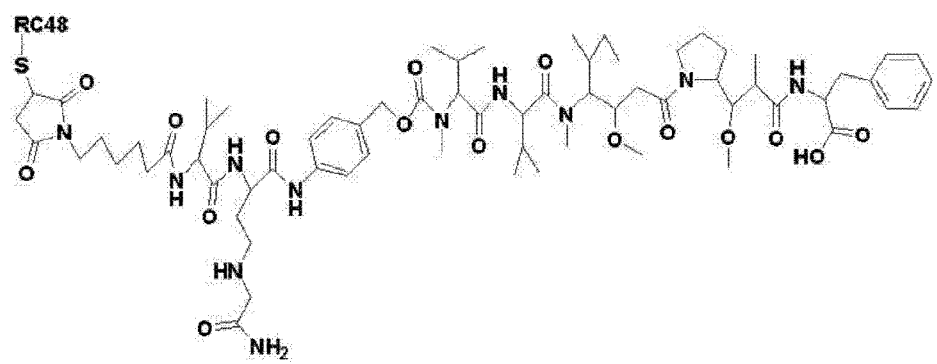
FIG. 9 shows the molecular structure of RC48 antibody-drug conjugate (RC48-vc-MMAF).
Figure 10:
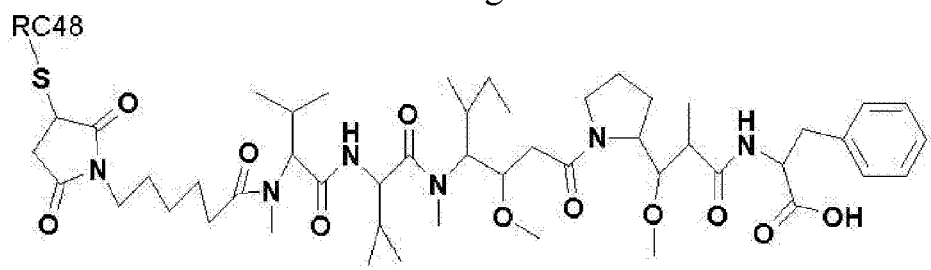
FIG. 10 shows the molecular structure of RC48 antibody-drug conjugate (RC48-mc-MMAF).

The binding capacities of Herceptin, cRC48, RC48 with different surface antigens EGFR, HER2, HER3 and HER4 were determined by ELISA method. The ELISA method could be found in Example 1. The 96-well plate was coated with antigens EGFR, HER2, HER3, HER4, respectively, each well of which was loaded with 20 ng, and incubated with different anti-HER2 antibodies, i.e., Herceptin, cRC48, RC48 antibodies, and then detected by horse radish peroxidase-coupled goat F(ab')2 anti-murine IgG Fc specific second antibody (Invitrogen Inc.). The result was shown in FIG. 5, indicating that Herceptin, cRC48, RC48 antibodies nearly had no binding capacity with EGFR, HER3 and HER4, but had a strong binding capacity with HER2, suggesting that Herceptin, RC48 highly specific binding with HER2.

Example 5 Assay for Tumor Inhibition of RC48 Towards BT474 Human Breast Cancer Transplantation Tumor Model Human breast cancer BT474 nude mouse transplantation tumor model was established by inoculating BT474 cells into nude mouse subcutaneously. After growing continuously in vivo for 3 generations, the tumor tissue which grew vigorously was taken and cut into about 1.5 mm3, and inoculated subcutaneously to right-side armpit of nude mouse (provided by Shanghai Slac Laboratory Animal Co. Ltd., with the certificate No. 2007000540582 and license No. SCXK(hu)2012-0002) under sterile conditions. The diameter of the nude mouse transplantation tumor was measured by vernier caliper. The animals were grouped randomly until the tumor grew up to 100~300 mm3. The tested drugs huIgG1, Herceptin, RC48 (each 10 mg/kg) were administered, and one week later dosed for the second time, and another two weeks later dosed for the third time, that is, the drugs were administered totally for three times.

Figure 11:
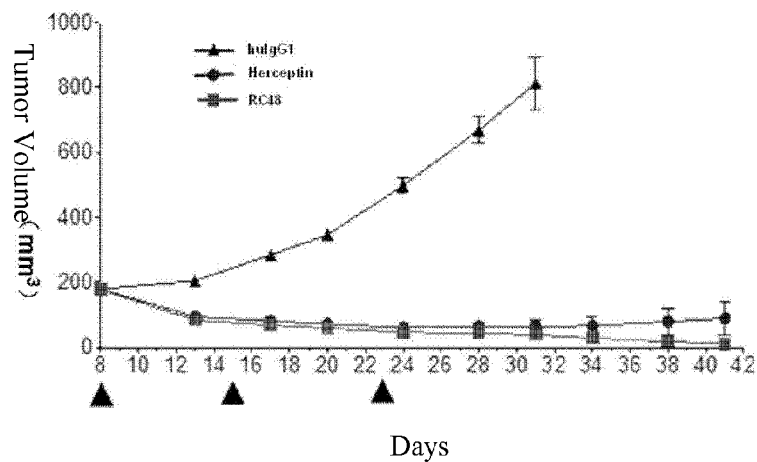
FIG. 11 shows the antitumor effect of RC48 directed to BT474 human breast cancer transplanation tumor model.

The result was shown in FIG. 11. After administrating huIgG1, the tumor was not inhibited, and the volume of which still continuously grew. After administrating Herceptin and RC48, the BT474 tumors were both inhibited. Compared with Herceptin, RC48 had a significantly better tumor-inhibitory effect.

Example 6 Preparation of Antibody Drug Conjugate

1) Purification of the Monoclonal Antibody RC48

The RC48 monoclonal antibody was captured from CHO cell culture by Protein A, which was then subjected to SDS-PAGE electrophoresis, with the purity up to 95% or higher by SEC analysis. The obtained antibody proteins were ultrafiltration dialyzed into PBS buffer by using 30KD membrane package, concentrated, and the concentration was calibrated by ultraviolet spectrometer, for the subsequent coupling reaction.

2) Coupling of Monoclonal Antibody RC48 with Drug Molecule

The reductive agent and protective agent were formulated with PBS buffer as follows: 1~20 mmol/L TCEP (Tris-2-carboxyethyl-phosphine), 1~20 mmol/L DTPA (Diethylene triamine pentacetate acid) stock solution, the reductive agent which may be added in a certain range of concentrations with the amount depending on the required drug antibody ratio, mixed with the monoclonal antibody at a certain concentration (e.g., 5~30 mg/ml) with a certain volume ratio (e.g., 1:1), in which the molar ratio of the final concentration of TCEP to the antibody was 0.5~6.0:1, and the reaction was performed with stirring for 2 h at 25° C. The free thiol concentration was detected at 412 nm by DTNB method, and calculated the numbers of free thiol with the molar ratio of antibody. The reductive reaction with TCEP had a very good reproducibility, and the numbers of free thiol could reach 1.0-8.0 after reduction.

After reduction with TCEP, the antibody may be directly subjected to subsequent conjugating. Drugs (vc-MMAE, vc-MMAF, mc-MMAF) (purchased from Shanghai Haoyuan Chemexpress Co. Ltd.) at a certain concentration (10 mM) were dissolved in 25% DMSO (dimethyl sulfoxide), for which the drugs were added slowly in the molar ratio of the drug to thiol of 0.3~2.8:1, and the reaction was performed with stirring for 2 h at 25° C. The free thiol concentration (close to zero) was detected at 412 nm by DTNB method, the residual unreacted drugs and free small molecules such as DMSO were removed by Sephadex G-25 purification, and the coupling condition was determined by SDS-PAGE electrophoresis, reversed-phase high performance liquid chromatography (R-HPLC) and Hydrophobic high performance liquid chromatography (HIC-HPLC) methods.

Example 7 Affinity Assay of ADC

Affinity Assay by ELISA Method

The ELISA plate was coated with recombinant protein HER2-ECD (with the concentration of 0.5 mg/ml), overnight at 2-8° C. The plate was washed for 3 times with the wellwash. At 37° C., 3% BSA-PBST solution was used for blocking for 2 h. The plate was washed for 3 times with the wellwash. The samples were loaded as follows: at 37° C., 11 spots were gradiently diluted from 1000 ng/ml (standard line) with PBST solution, 100 μl/well, for 2 h. The plate was washed for 3 times with the wellwash. The second antibody (goat anti-human IgG-Fc-HRP) was diluted 5000-fold with PBST solution. The colour developing reagent TMB was added for color developing for 8-10 minutes away from light at room temperature. The reaction was stopped by 2M $H_2SO_4$, and read at 450/655 nm in the enzyme-labeled instrument. The result is shown in Table 6.

TABLE 6

Comparison of the affinity between the conjugates and T-DM1

| Sample | Affinity ng/ml | Molar equivalent pmol/L |
|---|---|---|
| RC48-vc-MMAE | 2.237 | 15.22 |
| RC48-vc-MMAF | 3.349 | 13.51 |
| RC48-mc-MMAF | 2.902 | 16.42 |
| T-DM1 | 2.376 | 15.16 |

As known from the results, the affinities with HER2-ECD of RC48-vc-MMAE, RC48-vc-MMAF and RC48-mc-MMAF are comparable to that of T-DM1.

Example 8 Inhibitory Effect of the RC48 ADC on Tumor Cells

The well-grown cells were digested with trypsin (purchased from Sigma), after which the HER2 positive breast cancer cell SK-BR-3, HER2 positive ovary cancer cell SK-OV-3 were resuspended with DMEM medium containing 10% fetal bovine serum, McCoy's 5A medium (both of the mediums were purchased from Gibco), and inoculated into 96-well plate at the density of 5000, 4000 cells/well, respectively, and incubated in the incubator at 37° C., in 5% $CO_2$ for 24 h. RC48, Herceptin, RC48-vc-MMAE, RC48-vc-MMAF, RC48-mc-MMAF and T-DM1 (self-made) were diluted with the medium containing 10% fetal bovine serum at the concentrations as shown in the following figure before added into 96-well plate. After being incubated in the incubator at 37° C., in 5% $CO_2$ for 72 h, the detection was carried out by using CCK-8 kit (purchased from DOJINDO), and the resulted data were subjected to a statistic analysis using Prism software.

Figure 12:
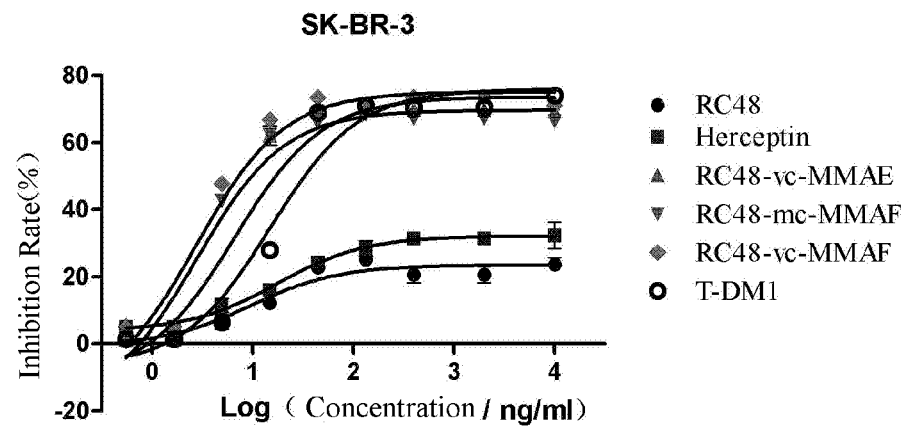
FIG. 12 shows the growth inhibiting effect of RC48 conjugate directed to HER2-positive cell SK-BR-3.
Figure 13:
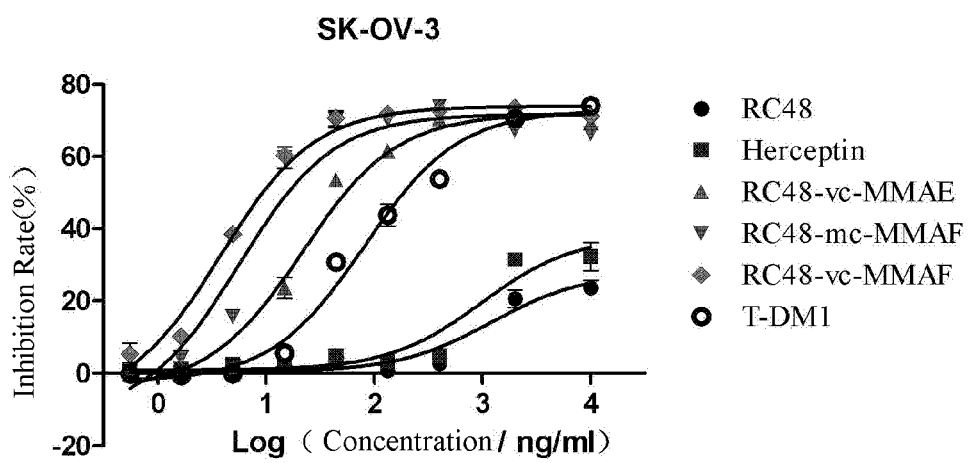
FIG. 13 shows the growth inhibiting effect of RC48 conjugate directed to HER2-positive cell SK-OV-3.

The results were shown in FIG. 12 to FIG. 13, as known from which the ADC drug of the present invention had a significantly stronger inhibitory effect towards various cells than naked antibody drug at the same concentration, and the inhibition rate directed to cell proliferation could be increased by a half. The ADC drug coupled with MMAF according to the present invention had a stronger inhibitory effect directed to SK-BR-3, SK-OV-3 cells than the ADC drug coupled with MMAE according to the present invention, nevertheless, both of which had significantly better effects than the positive control T-DM1.

Example 9 Anti-Tumor Activity of the Antibody Drug Conjugates Directed to Breast Cancer 1) Anti-Tumor Experiment of RC48 Conjugates Directed to BT474 Human Breast Cancer Tumor-Bearing Nude Mouse Model Five millions of BT474 cells were suspended in PBS, and inoculated to the armpit of BALB/c nude mouse (provided by Shanghai Slac Laboratory Animal Co. Ltd., with the certificate No. 2007000540582 and license No. SCXK(hu) 2012-0002). After the tumor was formed, the tumor tissue which grew vigorously was taken and cut into about 1.5 $mm^3$, and inoculated subcutaneously to the right-side armpit of nude mouse under sterile conditions. The diameter of the nude mouse transplantation tumor was measured by vernier caliper. The animals were grouped randomly until the tumor grew up to 100~300 $mm^3$. The tested drugs RC48 10 mg/kg, RC48-vc-MMAE 10 mg/kg, RC48-vc-MMAF 10 mg/kg and RC48-mc-MMAF 10 mg/kg were administered, and the drugs were administered totally for three times; the negative control group was administrated with equal amount of physiological saline.

Figure 14:
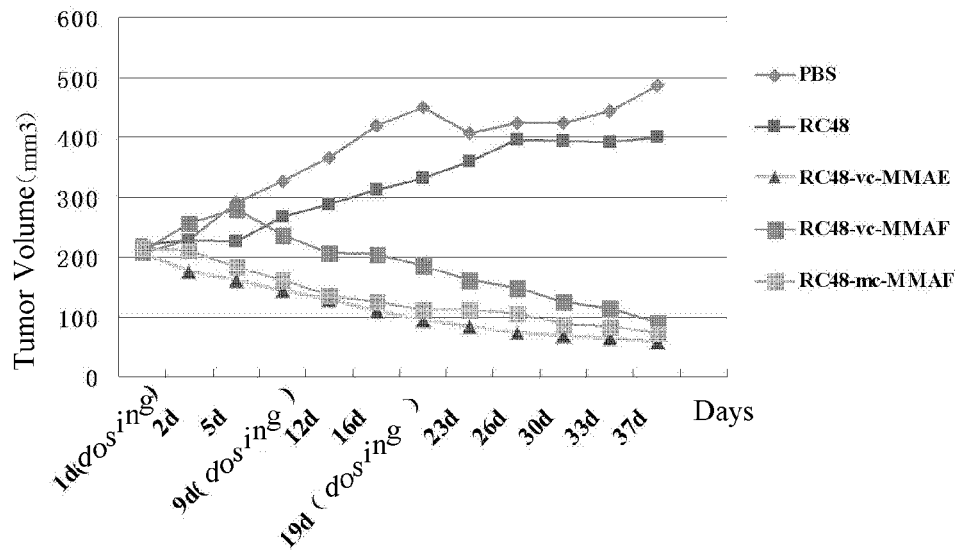
FIG. 14 shows the antitumor effect of RC48 conjugate directed to BT474 human breast cancer tumor bearing nude mouse model.

As shown in FIG. 14, 37 days after dosing, the tumor volume of the negative control group reached to 485 mm$^3$, while the tumor volume of RC48 group is 83% of the control group, which indicated that RC48 had the inhibitory effect to some extent on BT474 tumor growth. All of the three antibody conjugates tested in the present experiment (RC48-vc-MMAE, RC48-vc-MMAF, RC48-mc-MMAF) could inhibit BT474 tumor growth significantly, and 37 days after dosing, the tumor volumes shrank to 13-19% of the control group. During the 37-day experiment, there were 3 mice dead in the control group, while all of the mice in RC48-vc-MMAE group survived.

2) Anti-Tumor Experiment of RC48-Vc-MMAE Directed to Herceptin®- and Lapatinib-Resistant BT-474/L1.9 Human Breast Cancer Nude Mouse Subcutaneously-Transplantation Tumor Model BT474/L1.9 is BT-474 cell which has been treated for a long time with Herceptin® and Lapatinib, and also resistant to Herceptin® and Lapatinib.

SPF-level BALB/c nude mice were inoculated subcutaneously with a certain amount of BT-474/L1.9 tumor cells, and after the tumor growing to 100-200 mm3, the animals were randomly grouped. The dose was indicated by the legends: for RC48-vc-MMAE, Kadcyla™ (purchased from Roche Pharmaceuticals), dosing once per week, totally 2 times; for Herceptin® (purchased from Roche Pharmaceuticals), dosing once per week, totally 3 times; for Lapatinib (purchased from GSK), dosing everyday. The tumor volume was measured 2 times a week. The murine weight was weighted and the resistant capacity of the tumor-bearing mice towards the drugs was observed. The data were recorded. The tumor volume and the tumor-inhibition rate of each tumor-bearing mouse were calculated at different observation time points.

Figure 15:
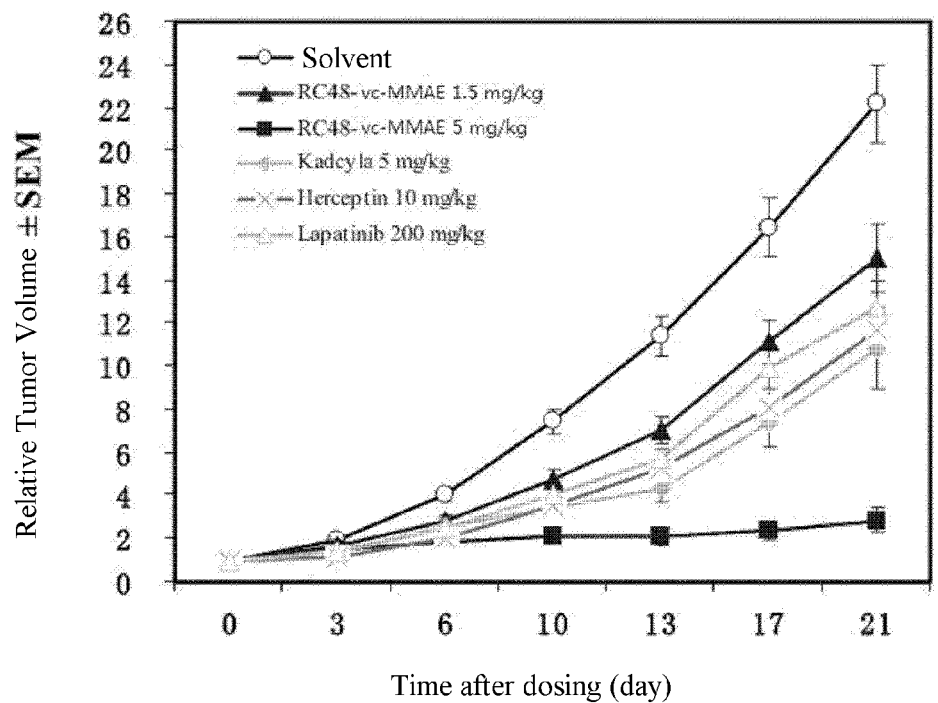
FIG. 15 shows the therapeutic effects of RC48-vc-MMAE, T-DM1 directed to Herceptin- and Lapatinib-resistant human breast cancer BT-474/L1.9 nude mouse transplantation tumors.

As shown in FIG. 15, the tumor-inhibition rate of Herceptin® (10 mg/kg) towards BT474/L1.9 nude mouse subcutaneous transplantation tumor was 51%; the tumor-inhibition rate of Lapatinib (200 mg/kg) towards BT474/L1.9 was 45%; it suggested that breast cancer BT474/L1.9 was resistant to both Herceptin® and Lapatinib. RC48-vc-MMAE (1.5, 5 mg/kg) inhibited the growth of BT474/L1.9 nude mouse subcutaneous transplantation tumor in a dose-dependent way, with the tumor-inhibition rate of 38% and 91% respectively; the tumor-inhibition rate of the reference drug Kadcyla™ (5 mg/kg) towards BT474/L1.9 nude mouse subcutaneous transplantation tumor was 58%, indicating that BT474/L1.9 was also resistant to Kadcyla™. The tumor-bearing mice were well resistant to all of the above drugs.

In conclusion, the ADC of the present invention shows a significant anti-tumor activity towards BT474/L1.9 cell nude mouse subcutaneous transplantation tumor model, which is significantly stronger than Herceptin and Lapatinib (p<0.01); compared with Kadcyla™ with the same dose of 5 mg/kg, the tumor-inhibitory effect of RC48-vc-MMAE of the present invention has an evident advantage (p<0.01), with the tumor-inhibition rate of 91%: 58%.

Example 10 The Anti-Tumor Activity of the Drug Conjugates Towards Ovary Cancer

1) Tumor-Inhibitory Experiment of RC48 Conjugates Towards SK-OV-3 Human Ovary Cancer Transplantation Tumor Model Human ovary cancer SK-OV-3 nude mouse transplantation tumor model was established by inoculating SK-OV-3 cells into nude mouse (provided by Shanghai Slac Laboratory Animal Co. Ltd., with the certificate No. 2007000540582 and license No. SCXK(hu)2012-0002) subcutaneously. The animals were grouped randomly until the tumor grew up to 100~300 mm$^3$. The tested drugs RC48 10 mg/kg, T-DM1 10 mg/kg, RC48-vc-MMAE 3 mg/kg, RC48-vc-MMAE 10 mg/kg, RC48-vc-MMAF 3 mg/kg, RC48-vc-MMAF 10 mg/kg, RC48-mc-MMAF 3 mg/kg and RC48-mc-MMAF 10 mg/kg were administered, dosing once per week, totally dosing 3 times; paclitaxel 10 mg/kg, 3 times per week, totally 3 weeks; meanwhile, the negative control was administrated with equal amount of physiological saline.

Figure 16:
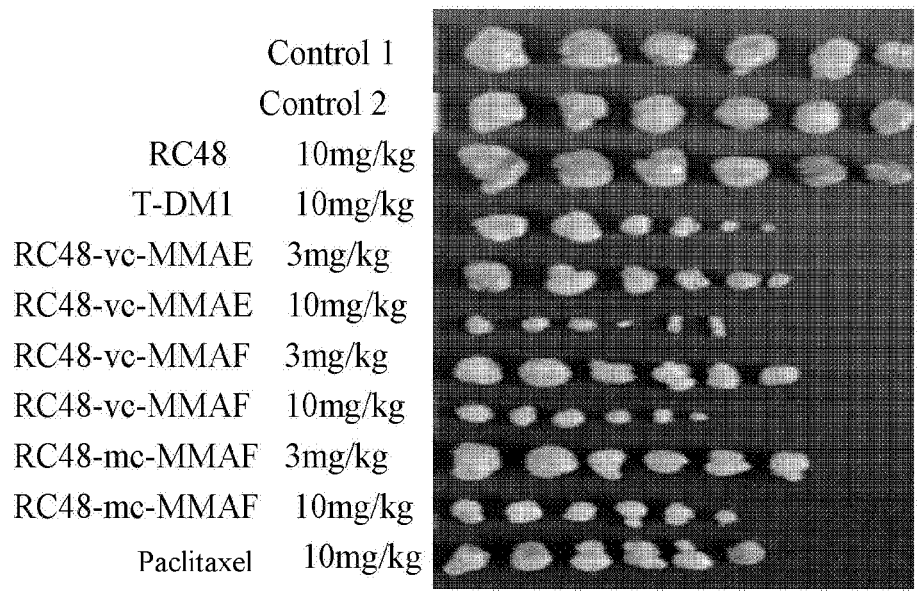
FIG. 16 shows the antitumor effect of RC48 conjugate directed to SK-OV-3 human ovary cancer transplantation tumor model.

The tumor-inhibitory effects of RC48 linked with different linkers and therapeutic agents on SK-OV-3 suggest that: compared with naked antibody RC48 which is not coupled, all of the ADCs of the present invention have good tumor-inhibitory effects; compared with T-DM1 in the same dose of 10 mg/kg, the tumor-inhibitory effects of RC48 conjugates of the present invention have evident advantages. The detailed results are shown in FIG. 16.

Example 11 Tumor-Inhibitory Experiment of Drug Conjugates Towards HER2 Positive NCI-N87 Human Gastric Cancer Cell Nude Mouse Subcutaneous Transplantation Tumor Model Human gastric cancer NCI-N87 cells highly expressed HER2 and EGFR, which was resistant to Herceptin®, and the model was established with the same method as Example 9. The result was shown in FIG. 17.

Figure 17:
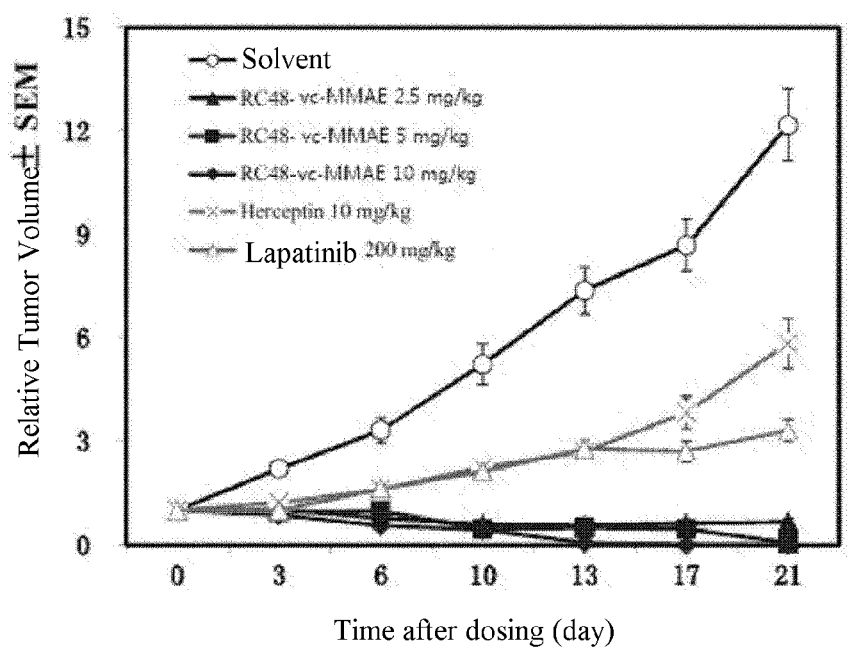
FIG. 17 shows the therapeutic effects of RC48-vc-MMAE, Herceptin, Lapatinib directed to human gastric cancer NCI-N87 nude mouse transplantation tumors.

As shown in FIG. 17, single intravenous injection of RC48-vc-MMAE (2.5, 5, 10 mg/kg) could significantly inhibit growth of HER2 highly expressed human gastric cancer NIC-N87 nude mouse subcutaneous transplantation tumor, with the tumor-inhibition rate of 133%, 193% and 200%. Low dose group caused partial regression of tumors in 6/6 mice; middle dose group caused partial regression of tumors in 1/6 mouse and complete regression in 5/6 mice; high dose group caused complete regression of tumors in all (6/6) mice, which did not relapse till the experiment ended (D21). The reference drug Herceptin® (10 mg/kg, dosing once per week, for 3 times) could inhibit growth of NCI-N87 nude mouse subcutaneous transplantation tumor, with the tumor-inhibition rate only of 49%; another reference drug small molecule EGFR/HER2 inhibitor Lapatinib (200 mg/kg, dosing once per week, for 21 days) had effect on NCI-N87 nude mouse subcutaneous transplantation tumor, with the tumor-inhibition rate of 78%. The tumor-bearing mice were resistant to all of the above drugs, and no symptoms such as loss of body weight occurred.

This research result indicates: 1) single intravenous injection of RC48-vc-MMAE (2.5, 5, 10 mg/kg) can significantly inhibit growth of HER2 highly expressed human gastric cancer NIC-N87 nude mouse subcutaneous transplantation tumor, causing partial or even complete regression of tumors; 2) the therapeutic effect of RC48-vc-MMAE towards NCI-N87 nude mouse subcutaneous transplantation tumor is evidently stronger than that of the reference drugs Herceptin® and Lapatinib (p<0.01).

Example 12 The Mouse Tolerance Assay of RC48 Conjugates

Figure 18:
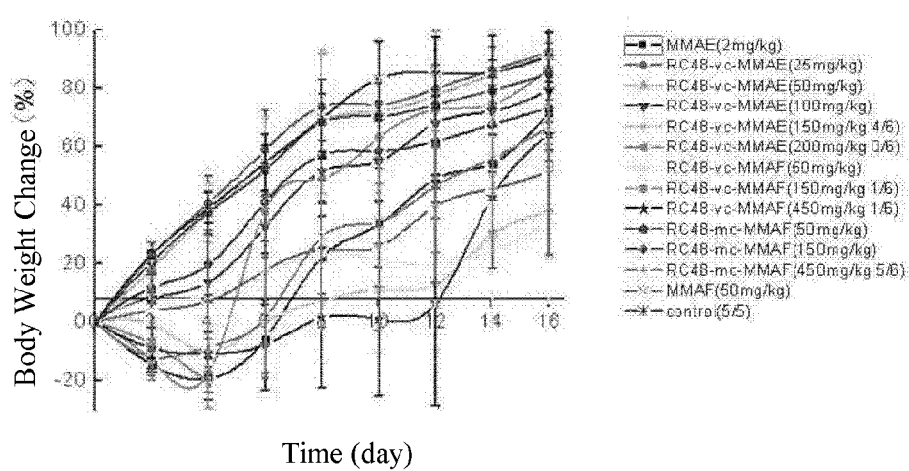
FIG. 18 shows the effect of different antibody-drug conjugates on mouse body weights.

The male and female KM mice which passed quarantine inspection were randomly divided into the following dose groups according to body weights: MMAE 2 mg/kg, MMAF 50 mg/kg, RC48-vc-MMAE 25 mg/kg (the corresponding MMAE dose was 0.5 mg/kg) 200 mg (the MMAE dose was 4.0 mg/kg), RC48-vc-MMAF 50 mg/kg (the MMAF dose was 1.0 mg/kg) 450 mg/kg (the MMAF dose was 9.0 mg/kg) and RC48-mc-MMAF 50 mg/kg (the MMAF dose was 1.0 mg/kg) 450 mg/kg (the MMAF dose was 9.0 ml/kg), in which there were 13 groups of different doses, with half male and half female, and the corresponding drug fluids were intravenously injected. Groups of mice in the same batch were used as the control groups, which were given with 0.9% NaCl injections of the same volume via tail vein. After dosing, the body weight was weighted once every other day, until Day 16. The body weight increasing curve of MMAE or MMAF serial mice could be found in FIG. 18 respectively.

The experiment result indicates: under the conditions of the present experiment, the toxicity of RC48-vc-MMAE is lower than uncoupled MMAE at the same dose. The maximal tolerant dose of mouse towards RC48-vc-MMAE is between 100 mg/kg (the MMAE dose is 2.0 mg/kg) and 150 mg/kg (the MMAE dose is 3.0 mg/kg).

The toxicity of RC48-vc-MMAF is evidently higher than that of RC48-mc-MMAF at the same dose. The maximal tolerant dose of mouse towards RC48-vc-MMAF is between 50 mg/kg (the MMAF dose is 1.0 mg/kg) and 100 mg/kg (the MMAF dose is 2.0 mg/kg). The MTD of mouse towards RC48-mc-MMAF is between 150 mg/kg (the MMAF dose is 3.0 mg/kg) and 450 mg/kg (the MMAF dose is 9.0 mg/kg).

Example 13 The Toxicity Experiment of the Drug Conjugates Towards SD Rat Dosed Via Single Intravenous Infusion SPF-level SD rats (the certificate No. is SCXK (jing) 2012-0001) purchased from Beijing Vital River Laboratories Animal Technology Co, Ltd. were randomly divided into 7 groups according to gender, in which there were 10 rats in a group with half male and half female. These 7 groups included physiological saline negative control group, 0.48 mg/kg MMAE control group, 40 mg/kg RC48 naked antibody control group and series of RC48-vc-MMAE dose groups, in which the rats were dosed via tail vein infusion, and the experimental observation period was 21 days. The body weights were weighted at D1 (pre-dosing), D8, D15 and D22. After the observation period, the animals were euthanized and performed a general pathological anatomical observation, and the abnormal tissues or organs observed by the general anatomical observation were subjected to a histological examination.

The death conditions of animals: 9/10 animals (MMAE control group), 1/10 animal (RC48-vc-MMAE, 30 mg/kg group) and 2/10 animals (RC48-vc-MMAE, 40 mg/kg group) were found dead during the experiments, while the remaining groups of animals were not found dead or in agonal state.

Under the conditions of the present experiment, the lethal dose of RC48-vc-MMAE towards rat was 30 mg/kg, and maximal tolerant dose was greater than or equaled to 24 mg/kg (the corresponding coupled MMAE dose was 0.48 mg/kg). RC48 naked antibody was given to SD rat with the dose of 40 mg/kg via single intravenous infusion, and there was no evident toxicity response symptom, suggesting the maximal tolerant dose of rat was greater than or equaled to 40 mg/kg. This result showed that, even if the conjugate of the present invention was used with a dose much higher than that of unconjugated drug MMAE (40 mg/kg vs 0.48 mg/kg), it still showed a toxicity much lower than that of the unconjugated drug MMAE, demonstrating that upon forming ADC by coupling MMAE with antibody, the toxicity decreased significantly.

The above as described is just the preferable embodiments, which are only regarded as examples while not limiting combination of the necessary features for carrying out the present invention. The subtitle as provided is not meant to limit various embodiments of the present invention. The terms such as "comprise", "contain" and "include" are not meant to limit. Furthermore, unless otherwise indicated, the term without numeral modification includes the plural forms thereof, and "or" means "and/or". Unless otherwise defined in the context, all of the technological and scientific terms as used herein have the same meanings as understood by those skilled in the art.

All of the publications and patents as mentioned in the present application are incorporated herein by reference. Without departing from the scope and spirit of the present invention, various modifications and variants of the methods and compositions described in the present invention are apparent to those skilled in the art. Although the present invention is described through particular preferable embodiments, it should be understood that the present invention should not be unsuitably limited to these particular embodiments. In fact, various variants, which are apparent for those skilled in the art for carrying out the modes described by the present invention, are intended to be included in the scope of the appended claims.

REFERENCES

[1] Nahta, R. and F. J. Esteva (2007). Trastuzumab triumphs and tribulations. Oncogene 6(25) 3637-43.
[2] Chen, Y. Z. et al. Expressions and Significance of HER2/neu protein in Epithelial Ovarian Carcinoma and its Metastatic lesions. Chinese General Practice, 2009, 12:1268-1271. (Chinese)
[3] Huang, X. E. The Study on the expression of HER2 and its correlation with the prognosis of breast carcinoma. Clinical Research, 2008, 49:39-40. (Chinese)
[4] de Bono J S, Bellmunt J, Attard Droz J P, Miller K, Flechon A, Sternberg C, Parker C, Zugmaier G, Hersberger-Gimenez V, Cockey L, Mason M, Graham J Open-label phase II study evaluating the efficacy and safety of two doses of pertuzumab in castrate chemotherapy-naive patients with hormone-refractory prostate cancer. J Clin Onco, 2007, Jan. 20; 25 (3):257-62
[5] Petersdorf S H, Kopecky K J, Slovak M, Willman C, Nevill T, Brandwein J, Larson R A, Erba H P, Stiff P J, Stuart R K, Walter R B, Tallman M S, Stenke L, Appelbaum F R. A phase III study of gemtuzumab ozogamicin during induction and post-consolidation therapy in younger patients with acute myeloid leukemia. Blood. 2013 Apr. 16.
[6] de Vries J F, Zwaan C M, De Bie M, Voerman J S, den Boer M L, van Dongen J J, van der Velden V H. The novel calicheamicin-conjugated CD22 antibody inotuzumab ozogamicin (CMC-544) effectively kills primary pediatric acute lymphoblastic leukemia cells. Leukemia. 2012 February; 26(2):255-64.
[7] Katz J, Janik J E, Younes A. 2011 Brentuximab Vedotin (SGN-35). Clin Cancer Res. 2011 Oct. 15; 17(20):6428-36.
[8] Girish S, Gupta M, Wang B et al. Clinical pharmacology of trastuzumab emtansine (T-DM1): an antibody-drug conjugate in development for the treatment of HER2-positive cancer. Cancer Chemotherapy and Pharmacology 2012; 69:1229-40.
[9] Lewis Phillips G D, Li G, Dugger D L et al. Targeting HER2-Positive Breast Cancer with Trastuzumab-DM1, an Antibody-Cytotoxic Drug Conjugate. Cancer Research 2008; 68: 9280-90.
[10] Krop I E, Beeram M, Modi S et al. Phase I Study of Trastuzumab-DM1, an HER2 Antibody-Drug Conjugate, Given Every 3 Weeks to Patients With HER2-Positive Metastatic Breast Cancer. Journal of Clinical Oncology 2010; 28: 2698-2704.
[11] Baselga J. Treatment of HER2-overexpressing breast cancer. Annals of Oncology 2010; 21: vii36-vii40.
[12] Joseph A. Francisco, Charles G. Cerveny, Damon L. Meyer, Bruce J. Mixan, Kerry Klussman, Dana, F. Chace, Starr X. Rejniak, Kristine A. Gordon, Ron DeBlanc, Brian E. Toki, Che-Leung Law, Svetlana O. Doronina, Clay B. Siegall, Peter D. Senter and Alan F. Wahl. 2003 cAC10-vcMMAE, an anti-CD30-monomethyl auristatin E conjugate with Potent and selective antitumor activity. Blood. 2003 102: 1458-1465.
[13] Dosio F P. Brusa and L Cattel. 2011 Immunotoxins and anticancer drugs conjugate assemblies: the role of the linkage between components. Toxins 3: 848-883.
[14] Concortis Biosystems Corp. USA www.concortisbiosystems.com
[15] CN1993146A

The invention claimed is:

1. An antibody or functional fragments thereof which can specifically bind to HER2, wherein the antibody comprises a heavy chain and a light chain, in which:
   (i) the heavy chain comprises three CDR regions, wherein the CDR regions have the amino acid sequence as shown in SEQ ID NO: 1, 2 and 3, respectively; and
   (ii) the light chain comprises three CDR regions, wherein the CDR regions have the amino acid sequence as shown in SEQ ID NO: 4, 5 and 6, respectively.

2. The antibody or functional fragments thereof according to claim 1, wherein the antibody is an antibody secreted from the hybridoma cells which were deposited at the China General Microbiological Culture Collection Center on Aug. 22, 2013, with the deposit number of CGMCC No. 8102.

3. The antibody or functional fragments thereof according to claim 1, wherein the antibody is a humanized antibody.

4. The antibody or functional fragments thereof according to claim 1, wherein the antibody is secreted from the CHO cells which were deposited at the China Center for Type Culture Collection on Nov. 6, 2013, with the deposit number of CCTCC C2013170.

5. An isolated polynucleotide, which encodes the antibody or functional fragments thereof according to claim 1.

6. A combination of the isolated polynucleotides, which comprises: a polynucleotide encoding the light chain of the antibody or functional fragments thereof according to claim 1 and a polynucleotide encoding the heavy chain of the antibody or functional fragments thereof according to claim 1.

7. A conjugate, which comprises the antibody or functional fragments thereof according to claim 1 which are conjugated with one or more therapeutic agents.

8. The conjugate according to claim 7, wherein the therapeutic agent is coupled with the antibody or the functional fragments thereof through a linker Previously presented.

9. The conjugate according to claim 7, wherein the conjugate has the general formula of Ab-(L-U)n, in which Ab represents the antibody or functional fragments thereof according to claim 1, L represents a linker, U represents a therapeutic agent, and n represents an integer from 1 to 8.

10. A pharmaceutical composition, which comprises the antibody or functional fragments thereof according to claim 1 and/or the conjugate according to claim 7, as well as a pharmaceutically acceptable carrier.

11. The conjugate according to claim 7, wherein the therapeutic agent is selected from cytotoxic drug, immunopotentiators and radioactive isotopes.

12. The conjugate according to claim 7, wherein the therapeutic agent is selected from dolastatin and derivatives thereof.

13. The conjugate according to claim 7, wherein the therapeutic agent is selected from MMAE and MMAF.

14. The conjugate according to claim 8, wherein the linker is linked with the antibody through thiol.

15. The conjugate according to claim 8, wherein the linker is selected from mc-vc-pAB or mc.

16. A method for treating cancer, comprising administering the pharmaceutical composition according to claim 10 in a therapeutically effective amount to a subject in need thereof.

17. The method according to claim 16, wherein the cancer is HER2-positive cancer.

18. The method according to claim 17, wherein the cancer is breast cancer, ovary cancer or gastric cancer.

19. The method according to claim 17, wherein the cancer is Lapatinib- and/or trastuzumab-resistant breast cancer, ovary cancer or gastric cancer.

* * * * *

UNITED STATES PATENT AND TRADEMARK OFFICE
CERTIFICATE OF CORRECTION

PATENT NO. : 10,087,260 B2
APPLICATION NO. : 15/037104
DATED : October 2, 2018
INVENTOR(S) : Jianmin Fang et al.

It is certified that error appears in the above-identified patent and that said Letters Patent is hereby corrected as shown below:

In the Claims

In Claim 8, Column 33, Lines 53-54, delete "Previously presented".

Signed and Sealed this
Sixth Day of November, 2018

Andrei Iancu
*Director of the United States Patent and Trademark Office*